US007887783B2

(12) United States Patent
Zhao

(10) Patent No.: US 7,887,783 B2
(45) Date of Patent: Feb. 15, 2011

(54) $^{99m}$TC-LABELED 19 AMINO ACID CONTAINING PEPTIDE FOR USE AS PHOSPHATIDYLETHANOLAMINE BINDING MOLECULAR PROBE AND RADIOPHARMACEUTICAL

(75) Inventor: Ming Zhao, Brookfield, WI (US)

(73) Assignee: Medical College of Wisconsin, Milwaukee, WI (US)

( * ) Notice: Subject to any disclaimer, the term of this patent is extended or adjusted under 35 U.S.C. 154(b) by 116 days.

(21) Appl. No.: 12/401,584

(22) Filed: Mar. 10, 2009

(65) Prior Publication Data

US 2010/0040543 A1 Feb. 18, 2010

Related U.S. Application Data

(60) Provisional application No. 61/068,764, filed on Mar. 10, 2008.

(51) Int. Cl.
*A61K 51/00* (2006.01)
*A61M 36/14* (2006.01)
(52) U.S. Cl. .................. 424/1.69; 424/1.11; 424/1.65; 424/9.1
(58) Field of Classification Search .............. 424/1.11, 424/1.65, 1.69, 1.81, 1.85, 1.89, 9.1, 9.3, 424/9.4, 9.5, 9.6, 9.7, 9.8; 534/7, 10–16; 530/300, 317, 323, 327, 333, 334, 335, 336, 530/337, 338, 339, 340, 341, 342, 343
See application file for complete search history.

(56) References Cited

FOREIGN PATENT DOCUMENTS

WO 2004006847 A2 1/2004

OTHER PUBLICATIONS

Khaw BA et al., Acute myocardial infarct imaging with indium-111-labeled monoclonal antimyosin, Fab. J Nucl Med, 1987, 28:1671-8.
Khaw BA et al., Scintigraphic quantification of myocardial necrosis in patients after intravenous injection of myosin-specific antibody, Circulation, 1986, 74:501-8.
Ono M et al., (99m)Tc-HYNIC-derivatized ternary ligand complexes for (99m)Tc-labeled polypeptides with low in vivo protein binding, Nucl Med Biol. Apr. 2001, 28(3):215-24.
Audi S et al., Quantitative Analysis of 99mTc-C2A-GST Distribution In The Area-At-Risk After Myocardial Ischemia and Reperfusion Using A Compartmental Model, Nucl Med Biol, 2007, 34(8):897-905.
Aoki Y et al., A novel peptide probe for studying the transbilayer movement of phosphatidylethanolamine, J Biochem (Tokyo), 1994,116(2):291-297.
Babich JW, Fischman AJ, Effect of "co-ligand" on the biodistribution of 99mTc-labeled hydrazino nicotinic acid derivatized chemotactic peptides, Nucl Med Biol, 1995, 22(1):25-30.
Babich JW et al, Technetium-99m-labeled hydrazino nicotinamide derivatized chemotactic peptide analogs for imaging focal sites of bacterial infection, J Nucl Med, 1993, 34(11):1964-1974.
Bevers et al., Lipid trans location across the plasma membrane of mammalian cells, Biochim Biophys Acta., 1999, 1439(3):317-330.
Blankenberg FG et al., In vivo detection and imaging of phosphatidylserine expression during programmed cell death, Proc Natl Acad Sci USA, 1998, 95:6349-54.
Braunwald E et al, American College of Cardiology, American Heart Association, Committee on the Management of Patients With Unstable Angina, ACC/AHA 2002 guideline update for the management of patients with unstable angina and non-ST-segment elevation myocardial infarction—summary article: a report of the American College of Cardiology/American Heart Association task force on practice guidelines, Committee on the Management of Patients With Unstable Angina, J Am Coll Cardiol 2002;40:1366-74.
Edwards DS et al., New and versatile ternary ligand system for technetium radiopharmaceuticals: water soluble phosphines and tricine as coligands in labeling a hydrazinonicotinamide-modified cyclic glycoprotein IIb/IIIa receptor antagonist with 99mTc., Bioconjug Chem., 1997, 8(2):146-154.
Emoto et al., Exposure of Phosphatidylethanolamine on the Surface of Apoptotic Cells, 1997, Exp Cell Res 232 (2):430-434.
Fang W et al., SPECT Imaging of Myocardial Infarction Using 99mTc Labeled C2A Domain of Synaptotagmin I in a Porcine Ischemia Reperfusion Model, Nucl Med Biol, 2007, 34(8):917-23.
Freude B et al., Cardiomyocyte apoptosis in acute and chronic conditions, Basic Res Cardiol, 1998; 93:85-89.
Guder A et al., Posttranslationally modified bacteriocins—the lantibiotics, Biopolymers, 2000, 55(1):62-73.
Hayashi F et al, The structure of PA48009: the revised structure of Duramycin, J Antiboiot (Tokyo), 1990, 43 (11):1421-1430.
Haynes DA et al., "Occurrence of pharmaceutically acceptable anions and cations in the Cambridge Structural Database," J. Pharm. Sci. 94:2111-2120 (2005).
Hofstra L et al, Visualisation of cell death in vivo in patients with acute myocardial infarction, Lancet, 2000, 356:209-12.
Hosoda K et al., Structure determination of an immunopotentiator peptide, cinnamycin, complexed with lysophosphatidylethanolamine by 1H-NMR1, J Biochem (Tokyo), 1996, 119(2):226-230.

(Continued)

*Primary Examiner*—D L Jones
(74) *Attorney, Agent, or Firm*—Sara D. Vinarov

(57) ABSTRACT

With only 19 amino acids, Duramycin is the smallest known polypeptide that has a defined 3-dimensional binding structure. Duramycin binds Phosphatidylethanolamine (PtdE) at a 1:1 ratio with high affinity and exclusive specificity. As an abundant binding target, PtdE is a major phospholipid and accounts for about 20% of the phospholipid content in mammalian cellular membranes. PtdE is externalized to the surface of apoptotic cells, and also becomes accessible in necrotic cells due to compromised plasma membrane integrity. Given the unique physicochemical properties of Duramycin and the availability of PtdE in acute cell death, the goal of this study is to develop and evaluate $^{99m}$Tc-HYNIC-Duramycin as a novel molecular probe for imaging PtdE.

$^{99m}$Tc-HYNIC-Duramycin is a low-molecular weight, fast-clearing radiopharmaceutical that detects apoptosis/necrosis by binding to PtdE. The goal was to quantify the uptake of $^{99m}$Tc-HYNIC-Duramycin in the area-at-risk after myocardial ischemia and reperfusion, and to determine the window of detection.

24 Claims, 8 Drawing Sheets

OTHER PUBLICATIONS

Huber R et al., The crystal and molecular structure of human annexin V, an anticoagulant protein that binds to calcium and membranes, EMBO J, 1990, 9:3867-3874.

IUPAC-IUB Commission on Biochemical Nomenclature, Biochemistry (1972) 11:1726-1732.

Iwamoto K et al., Curvature-dependent recognition of ethanolamine phospholipids by Duramycin and Cinnamycin, Biophys J. 2007, 93(5):1608-1619.

Jung Hi et al., Detection of apoptosis using the C2A domain of synaptotagmin I, Bioconjugate Chem, 2004,15:983-7.

Kaletta C et al., Prepeptide sequence of cinnamycin (Ro 09-0198): the first structural gene of a Duramycin-type lantibiotic, Eur J Biochem, 1991, 199(2):411-415.

Khaw BA, The current role of infarct avid imaging, Semin Nucl Med, 1999, 29:259-70.

Kim RJ et al., Myocardial Gd-DTPA kinetics determine MRI contrast enhancement and reflect the extent and severity of myocardial injury after acute reperfused infarction, Circulation, 1996, 94:3318-3326.

Kostin S et al., Myocytes die by multiple mechanisms in failing human hearts, Circ Res, 2003, 92:715-724.

Krishnan AS et al., Detection of cell death in tumors by using MR imaging and a gadolinium-based targeted contrast agent, Radiology, Mar. 2008, 246(3):854-62.

Lahorte CM et al, Apoptosis-detecting radioligands: current state of the art and future perspectives, Eur J Nucl Med, 2004, 31:887-919.

Liu Z et al., In vivo dynamic imaging of myocardial cell death using 99mTc-labeled C2A domain of Synaptotagmin I in a rat model of ischemia and reperfusion, Nucl Med Biol, 2007, 34 (8):907-15.

Liu S et al., 99mTc-labeled small peptides as diagnostic radiopharmaceuticals, Chem Rev. 1999;99:2235-2268.

Liu S et al., 99mTc labeling of highly potent small peptides, Bioconjug Chem., 1997, 8(5):621-636.

Liu S et al., Labeling a hydrazino nicotinamide-modified cyclic IIb/IIIa receptor antagonist with 99m Tc using aminocarboxylates as coligands, Bioconjug Chem, 1996, 7(1):63-71.

Machaidze G et al., Specific binding of Ro 09-0198 (cinnamycin) to phosphatidylethanolamine: a thermodynamic analysis, Biochemistry, 2002, 41(6):1965-1971.

Marki F et al, Mode of action of the lanthionine-containing peptide antibiotics Duramycin, Duramycin B and C, and Cinnamycin as indirect inhibitors of phospholipase A2, Biochem Pharmacol., 1991, 42(10):2027-2035.

McNulty MJ et al., Pharmacokinetics and tissue distribution of the nonadecapeptide Moli1901 in rats and mice, Xenobiotica 2003;33(2):197-210.

Mills JC et al, Apoptotic membrane blebbing is regulated by myosin light chain phosphorylation, J Cell Biol, 1998, 140 (3):627-636.

Ohtsuki K et al., Technetium-99m HYNNIC-Annexin V: a potential radiopharmaceutical for the in-vivo detection of apoptosis, Eur J Nucl Med, 1999, 26:1251-58.

Petrovsky A et al., Near-infrared fluorescent imaging of tumor apoptosis, Cancer Res, 2003, 63:1936-42.

Pope JH et al, HP. Missed diagnoses of acute cardiac ischemia in the emergency department, N. Engl J Med 2000;342:1163-70.

Seelig J, Thermodynamics of lipid-peptide interactions, Biochim Biophys Acta., 2004, 1666(1-2):40-50.

Sosnovik et al., Magnetic resonance imaging of cardiomyocyte apoptosis with a novel magneto-optical nanoparticle, Magn Reson Med, Sep. 2005, 54(3):718-24.

Spector AA, Yorek MA, Membrane lipid composition and cellular function, J Lipid Res, 1985, 26(9):1015-1035.

Sutton RB et al., Structure of the first C2 domain of synaptotagmin I: a novel Ca2+/phospholipid-binding fold, Cell, 1995, 80:929-938.

Tait JF et al., Structural requirements for in vivo detection of cell death with 99mTc-Annexin V, J Nucl Med, 2005, 46 (5):807-815.

Taki J et al, Detection of cardiomyocyte death in a rat model of ischemia and reperfusion using 99mTc-labeled annexin V, J Nucl Med, 2004, 45:1536-41.

Thimister PW et al., In vivo detection of cell death in the area at risk in acute myocardial infarction, J Nucl Med, 2003, 44:391-6.

Umeda M et al, Membrane phospholipid dynamics during cytokinesis: regulation of actin filament assembly by redistribution of membrane surface phospholipid, Chem Phys Lipids, 1999, 101(1):81-91.

Zhao M et al., 99mTc-labeled Duramycin as a novel hosphatidylethanolamine-binding molecular probe, J Nucl Med 2008;49:1345-52.

Zhao M et al., 99mTc-labeled C2A domain of synaptotagmin I as a target-specific molecular probe for noninvasive imaging of acute myocardial infarction, J Nucl Med. 2006, 47(8):1367-1374.

Zhao M et al., Non-invasive detection of apoptosis using magnetic resonance imaging and a targeted contrast agent, Nat Med, 2001, 7:1241-44.

Zhu X et al., Imaging acute cardiac cell death: temporal and spatial distribution of 99mTc-labeled C2A in the area at risk after myocardial ischemia and reperfusion, J Nucl Med, 2007, 48:1031-6.

Zimmermann N. et al, Solution structures of the lantibiotics Duramycin B and C, Eur J Biochem, 1993, 216(2):419-428.

International Search Report and Written Opinion, mailed on Feb. 16, 2010 (International Application No. PCT/US2009/036692; filed Mar. 10, 2009).

SEQUENCE LISTING

<160> NUMBER OF SEQ ID NOS: 4

<210> SEQ ID NO 1
<211> LENGTH: 19
<212> TYPE: PRT
<213> ORGANISM: Streptoverticillium cinnamoneus

<400> SEQUENCE: 1

Cys Lys Gln Ser Cys Ser Phe Gly Pro Phe Thr Phe Val Cys Asp Gly
1               5                   10                  15

Asn Thr Lys

<210> SEQ ID NO 2
<211> LENGTH: 19
<212> TYPE: PRT
<213> ORGANISM: Streptoverticillium cinnamoneus

<400> SEQUENCE: 2

Cys Arg Gln Ser Cys Ser Phe Gly Pro Phe Thr Phe Val Cys Asp Gly
1               5                   10                  15

Asn Thr Lys

<210> SEQ ID NO 3
<211> LENGTH: 19
<212> TYPE: PRT
<213> ORGANISM: Streptoverticillium cinnamoneus

<400> SEQUENCE: 3

Cys Arg Gln Ser Cys Ser Phe Gly Pro Leu Thr Phe Val Cys Asp Gly
1               5                   10                  15

Asn Thr Lys

<210> SEQ ID NO 4
<211> LENGTH: 19
<212> TYPE: PRT
<213> ORGANISM: Streptoverticillium cinnamoneus

<400> SEQUENCE: 4

Cys Ala Asn Ser Cys Ser Tyr Gly Pro Leu Thr Trp Ser Cys Asp Gly
1               5                   10                  15

Asn Thr Lys

$^{99m}$TC-LABELED 19 AMINO ACID CONTAINING PEPTIDE FOR USE AS PHOSPHATIDYLETHANOLAMINE BINDING MOLECULAR PROBE AND RADIOPHARMACEUTICAL

CROSS REFERENCE TO RELATED APPLICATIONS

This application claims priority to and benefit of Patent Cooperation Treaty Application Serial No. PCT/US09/36692 filed Mar. 10, 2009. This application also claims priority to and benefit of U.S. Provisional Patent Application Ser. No. 61/068,764, filed on Mar. 10, 2008.

STATEMENT REGARDING GOVERNMENT INTEREST

Not applicable.

BACKGROUND OF THE INVENTION

The non-invasive imaging of acute cell death, including apoptosis and necrosis, has important implications in the assessment of degenerative diseases and in the monitoring of tumor treatments. The need to achieve better and earlier imaging necessitates continuous efforts to discover and development uptake mechanisms and molecular probes that provide improved binding, pharmacokinetic and biodistribution properties.

Technetium-99m ($^{99m}$Tc) is a gamma ray emitting isotope used in radioactive isotope medical tests, e.g., as a radioactive tracer that medical equipment can detect in the body. $^{99m}$Tc is well suited to the role because it emits readily detectable 140 keV gamma rays. The half-life of $^{99m}$Tc for gamma emission is 6.01 hours, which means that about fifteen sixteenths (93.7%) of it decays to $^{99}$Tc in 24 hours. The short half life of the isotope allows for scanning procedures which collect data rapidly, but keep total patient radiation exposure low.

$^{99m}$Tc decays to technetium-99 (Tc-99, a less excited state of the same isotope) by rearrangement of nucleons in its nucleus. Technetium-99 emits soft beta rays but no gamma rays.

Due to its short half-life, for nuclear medicine purposes, $^{99m}$Tc is usually extracted from technetium-99m generators which contain Mo-99, which is the usual parent nuclide for this isotope. The majority of Mo-99 produced for Tc-99m medical use comes from fission of HEU from only four reactors around the world: NRU, Canada; BR2, Belgium; SAFARI-1, South Africa; and HFR, the Netherlands. Production from LEU is possible, and is proposed at the new OPAL reactor, Australia, as well as other sites. Activation of Mo-98 is another, currently smaller, route of production. (CRP on Production of Mo-99 from LEU or Neutron Activation, IAEA)

$^{99m}$Tc is used in 20 million diagnostic nuclear medical procedures every year. Approximately 85 percent of diagnostic imaging procedures in nuclear medicine use this isotope. Depending on the type of nuclear medicine procedure, the Tc-99m is tagged (or bound to) a pharmaceutical that transports the Tc-99m to its required location. For example, when Tc-99m is chemically bound to Exametazime, the drug is able to be cross the blood brain barrier and flow through the vessels in the brain to see cerebral blood flow (it is also used for labeling white blood cells to visualize sites of infection). Tc-99m Sestamibi is used for myocardial perfusion imaging, which shows how well the blood flows through the heart. Measurements of renal function and imaging is undertaken by tagged to Mercapto Acetyl Tri Glycine, known as a MAG3 scan.

$^{99m}$Tc is made from the synthetic substance molybdenum-99 which is a by-product of nuclear fission. It is because of its parent nuclide, that $^{99m}$Tc is so suitable to modern medicine. Molybdenum-99 has a half-life of approximately 66 hours, and decays to $^{99m}$Tc, a negative beta, and an antineutrino:

where β−=a negative beta particle (electron), and ν=an antineutrino;

where β−=a negative beta particle (electron) and ν=an antineutrino, it will then undergo an isomeric transition to yield $^{99}$Tc and a monoenergetic gamma emission:

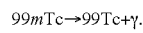

Single photon emission computed tomography known as SPECT is a nuclear medicine imaging technique using gamma rays. In the use of technetium-99m, the radioisotope is administered to the patient and the escaping gamma rays are incident upon a gamma camera which computes and calculates the image. To acquire SPECT images, the gamma camera is rotated around the patient. Projections are acquired at defined points during the rotation, typically every 3-6 degrees. In most cases, a full 360 degree rotation is used to obtain an optimal reconstruction. The time taken to obtain each projection is also variable, but 15-20 seconds is typical. This gives a total scan time of 15-20 minutes. The technetium-99m radioisotope is used predominantly in both bone and brain scans to check for any irregularities. Although Tc-99m is used for diagnostic nuclear medicine imaging procedures, it is not used for any therapeutic procedures.

SUMMARY OF THE INVENTION

One aspect of the invention is a radiopharmaceutical compound made by a process comprising the steps or acts of providing a polypeptide sequence set forth in SEQ. ID. No. 1 or a sequence having at least 70% sequence similarity to SEQ. ID. No. 1, wherein the polypeptide comprises a thioether bond between amino acids located at positions 1-18, 4-14, and 5-11, wherein the polypeptide comprises an amide bond between amino acids located at positions 6-19, and, wherein one or more distal moieties according to the structure

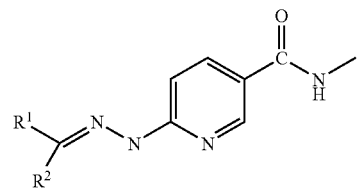

are covalently bound to the amino acid at position 1, position 2, or, positions 1 and 2 of the polypeptide, and, wherein $R^1$ and $R^2$ are each independently a straight or branched, saturated or unsaturated $C_{1-4}$ alkyl, and, chelating one or more of the distal moieties with $^{99m}Tc^x$, $(^{99m}Tc\!=\!\!O)^{+3}$, $(^{99m}Tc\!\equiv\!\!N)^{+2}$, $O\!=\!^{99m}Tc\!=\!\!O)^{+}$ or $(^{99m}Tc(CO)_3)^{+}$, wherein x is a redox or oxidation state selected from the group consisting of +7, +6, +5, +4, +3, +2, +1, 0 and −1, or, a salt, solvate or hydrate thereof.

In an exemplary embodiment of the radiopharmaceutical compound, $R^1$ is $CH_3$, and $R^2$ is $CH_3$.

In another exemplary embodiment of the radiopharmaceutical compound, the compound according to SEQ. ID. No. 1 is substituted with the distal moiety at position 1.

In another exemplary embodiment of the radiopharmaceutical compound, the compound according to SEQ. ID. No. 1 is substituted with the distal moiety at position 2.

In another exemplary embodiment of the radiopharmaceutical compound, the compound according to SEQ. ID. No. 1 is substituted with distal moieties at positions 1 and 2.

In another exemplary embodiment of any one of the above radiopharmaceutical compounds, amino acids located at positions 7, 10, or 12, or a combination thereof, are substituted with a hydrophobic amino acid selected from Val, Leu, Ile, Met, or Trp, or a combination thereof.

In another exemplary embodiment of any one of the above radiopharmaceutical compounds, amino acids located at positions 8, 13 or a combination thereof are substituted with a hydrophobic amino acid selected from Val, Leu, Ile, Met, or Phe, or a combination thereof.

In another exemplary embodiment of any one of the above radiopharmaceutical compounds, at least one amino acid residue located at positions 1-4 and 16-19 of the polypeptide are modified by at least one modifier selected from a functional group, polymer, peptide, protein, complex, particle and liposome.

In another exemplary embodiment of any one of the above radiopharmaceutical compounds, the modified polypeptide substantially retains binding affinity and specificity towards phosphatidylethanolamine.

In another embodiment of any one of the above radiopharmaceutical compounds, the compound according to SEQ. ID. No. 1 is truncated or elongated, but substantially retains binding affinity and specificity towards phosphatidylethanolamine.

Another aspect of the invention is a pharmaceutical injectable dosage form comprising any one of the above radiopharmaceutical compounds, and, an injectable carrier system.

Another aspect of the invention is a method of imaging cardiac apoptosis and/or necrosis, atherosclerotic plaque or acute myocardial infarct comprising the steps or acts of administering any one of the above pharmaceutical dosage forms to a patient, and, imaging the gamma rays emitted by the $^{99m}Tc^x$.

Another aspect of the invention is a radiopharmaceutical compound made by a process comprising the steps or acts of providing a polypeptide sequence set forth in SEQ. ID. No. 1 or a sequence having at least 70% sequence similarity to SEQ. ID. No. 1, wherein the polypeptide comprises a thioether bond between amino acids located at positions 1-18, 4-14, and 5-11, wherein the polypeptide comprises an amide bond between amino acids located at positions 6-19, and, wherein one or more distal moieties according to the structure

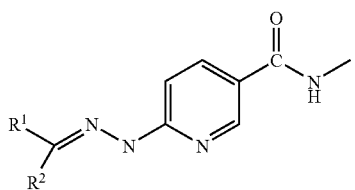

are covalently bound to the amino acid at position 1, position 2, or, positions 1 and 2 of the polypeptide, and, wherein $R^1$ and $R^2$ are each independently a straight or branched, saturated or unsaturated $C_{1-4}$ alkyl, and, chelating one or more of the distal moieties with an isotope selected from $^{111}In^{+3}$, $^{111}In^{0}$, $^{111}In^{-5}$, $^{125}I^{-1}$, $^{125}I^{0}$, $^{125}I^{+7}$, $^{131}I^{-1}$, $^{131}I^{0}$, $^{131}I^{+7}$, $^{18}F^{-1}$, $^{18}F^{0}$, $^{64}Cu^{0}$, $^{64}Cu^{+1}$, $^{64}Cu^{+2}$ or $^{64}Cu^{+3}$, or, a salt, solvate or hydrate thereof.

Another aspect of the invention is a pharmaceutical injectable dosage form comprising the above radiopharmaceutical compound, and, an injectable carrier system.

Another aspect of the invention is a method of imaging cardiac apoptosis and/or necrosis, atherosclerotic plaque or acute myocardial infarct comprising the steps or acts of administering the above pharmaceutical dosage form to a patient, and, imaging the gamma rays emitted by the isotope. Radiopharmaceutical compounds comprising the $^{18}F^{-1}$, $^{18}F^{0}$, $^{64}Cu^{0}$, $^{64}Cu^{+1}$, $^{64}Cu^{+2}$ or $^{64}Cu^{+3}$, isotopes are imaged using positron emission tomography (PET).

As used herein, Duramycin modified with 6-hydrazinopyridine-3-carboxylic acid (HYNIC), labeled with $^{99m}Tc$ and, chelated thereof is referred to as $^{99m}Tc$-HYNIC-Duramycin or similar nomenclature, whereby a

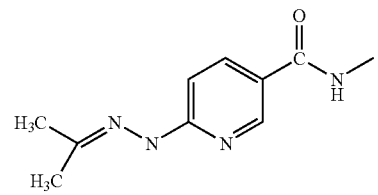

distal moiety is covalently bound to the 2-Lys.

Another aspect of the invention is a radiopharmaceutical compound wherein the $^{99m}Tc^x$ atom can be incorporated onto Duramycin by methods that vary in radiochemistry but consistent in the outcome of $^{99m}Tc$-tagging of Duramycin. These variations of $^{99m}Tc$ radiochemistry include the radioisotope at different redox states (+7, +6, +5, +4, +3, +2, +1, 0, and −1 oxidation state) and/or chelated with and without chelation cores and coligands. The resultant radiopharmaceutical compound is sufficiently stable for use as an imaging agent in a predetermined imaging device. The $^{99m}Tc$-Duramycin complex (with or without chelation cores and/or co-ligands) provides targeted delivery of radioactivity to tissues and organs via the binding activities of Duramycin. For radiolabeling, the technetium core may be a "naked" technetium atom, $^{99m}Tc$ (III) core, $^{99m}Tc(IV)$ core, $[^{99m}Tc=O]^{3+}$ core, $[^{99m}Tc\equiv N]^{2+}$ core, $[O=^{99m}Tc=O]^{+}$ core, $[^{99m}Tc(CO)_3]^{+}$ core or $[^{99m}Tc]$ HYNIC core. The chelation molecule may contain one or more mono-, bi- and multi-functional species that covalently or non-covalently bond to Duramcyin, and includes N-Hydroxysuccinimide (NHS) esters, isothiocyanates, maleimide, biotin, glutathione, antibodies, antigens and the like. The $^{99m}Tc$ chelation configuration may include $N_2S_4$, $N_2S_3$, $N_2S_2$ or $N_3S$. The variations among chelation groups may include natural and/or modified amino acids, such as different lengths and combinations of Gly-Ser-Cys, Gly-Gly-Cys, Cys-Gly-Cys, Lys-Gly-Cys, Gly-Ala-Gly, His-His-His, $MAG_3$, $MAG_2$-$NH_2$, Benzoyl-$MAG_3$, Methyl-$MAG_2$-$NH_2$, and the like. (MAG is Mercapto Acetyl Tri Glycine, a compound that is chelated with a radioactive element). Apart from the core radiochemistry for $^{99m}Tc$, there may be variations in coligands, whereby the common ones include tricine, phosphine compounds, dicine, bicine, glucoheptonate, EDDA (ethylenediamine-N,N'-diacetate), imine-N-heterocycle, PADA (pyridine-2-azo-p-dimethylaniline) and the like. Another aspect of the invention is a pharmaceutical injectable dosage form comprising any one of these radiopharmaceutical compounds, and, an injectable carrier system. Still another aspect is a method of imaging cardiac apoptosis and/or necrosis, atherosclerotic plaque or acute myocardial infarct comprising the steps or acts of administering any one of these pharmaceutical dosage forms to a patient, and, imaging the gamma rays emitted by the isotope. The radiochemistry of $^{99m}$Tc is found in Liu S et al., $^{99m}$Tc-labeled small peptides as diagnostic radiopharmaceuticals, *Chem. Rev.* 1999; 99:2235-2268, which is incorporated herein in its entirety.

Another aspect of the invention is a radiopharmaceutical compound made by a process comprising the steps or acts of providing a polypeptide sequence set forth in SEQ. ID. No. 1 or a sequence having at least 70% sequence similarity to SEQ. ID. No. 1, wherein the polypeptide comprises a thioether bond between amino acids located at positions 1-18, 4-14, and 5-11, wherein the polypeptide comprises an amide bond between amino acids located at positions 6-19, and, wherein one or more distal moieties according to the structure

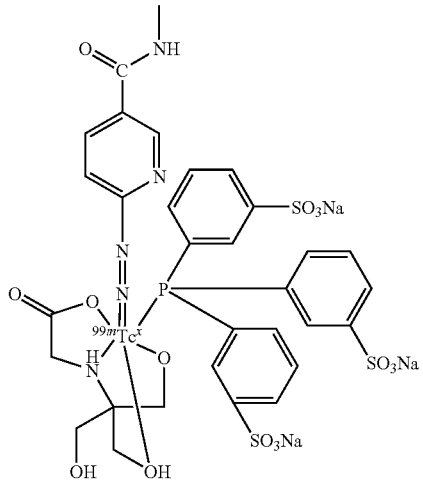

are covalently bound to the amino acid at position 1, position 2, or, positions 1 and 2 of the polypeptide, wherein x is a redox or oxidation state selected from the group consisting of +7, +6, +5, +4, +3, +2, +1, 0 and −1, or, a salt, solvate or hydrate thereof.

In an exemplary embodiment of the above radiopharmaceutical compound, the compound according to SEQ. ID. No. 1 is substituted with the distal moiety at position 1.

In another exemplary embodiment of the above radiopharmaceutical compound, the compound according to SEQ. ID. No. 1 is substituted with the distal moiety at position 2.

In another exemplary embodiment of the above radiopharmaceutical compound, the compound according to SEQ. ID. No. 1 is substituted with distal moieties at positions 1 and 2.

In another exemplary embodiment of the above radiopharmaceutical compound, amino acids located at positions 7, 10, or 12, or a combination thereof, are substituted with a hydrophobic amino acid selected from Val, Leu, Ile, Met, or Trp, or a combination thereof.

In another exemplary embodiment of the above radiopharmaceutical compound, amino acids located at positions 8, 13 or a combination thereof are substituted with a hydrophobic amino acid selected from Val, Leu, Ile, Met, or Phe, or a combination thereof.

In another exemplary embodiment of the above radiopharmaceutical compound, at least one amino acid residue located at positions 1-4 and 16-19 of the polypeptide are modified by at least one modifier selected from a functional group, polymer, peptide, protein, complex, particle and liposome.

In another exemplary embodiment of the above radiopharmaceutical compound, the modified polypeptide substantially retains binding affinity and specificity towards phosphatidylethanolamine.

Another aspect of the invention is a pharmaceutical injectable dosage form comprising any one of the above radiopharmaceutical compounds, and, an injectable carrier system.

Another aspect of the invention is a method of imaging cardiac apoptosis and/or necrosis, atherosclerotic plaque or acute myocardial infarct comprising the acts or steps of administering any one of the above pharmaceutical dosage forms to a patient, and, imaging the gamma rays emitted by the $^{99m}$Tc$^x$.

DESCRIPTION OF DRAWINGS OF
EXEMPLARY EMBODIMENTS

FIG. 1: Panel A includes a diagram illustrating the primary structure of Duramycin with cross-linking bridges, whereby radio-HPLC chromatograms of $^{99m}$Tc-HYNIC-Duramycin before and after purification are shown in Panel B and Panel C, respectively, whereby a low (but significant) level of technetium pertechnetate is present before purification with a retention time of 2 min, and, Panel D shows a representative competition curve out of three independent experiments, and, whereby $^{99m}$Tc-HYNIC-Duramycin binding of apoptotic cells is competitively diminished by the presence of PtdE-containing liposomes (●) but not other phospholipid species including PtdC (■), PtdG (□) or PtdS (○).

FIG. 2: Panel A shows blood clearance of $^{99m}$Tc-HYNIC-Duramycin in healthy rats (n=3), Panel B shows radio-HPLC chromatograms of $^{99m}$Tc-HYNIC-Duramycin standard, Panel C shows serum at 1 min after injection, Panel D shows serum at 5 min after injection, and, Panel E shows urine at 60 min after injection.

FIG. 3: Panel A shows dynamic planar imaging of $^{99m}$Tc-HYNIC-Duramycin distribution in a healthy rat, whereby the rapid renal clearance of the radiotracer and low hepatic uptake, Panel B shows whole-body dynamic planar imaging of $^{99m}$Tc-HYNIC-Duramycin uptake in a rat with acute myocardial infarction, and, Panel C shows non-color-enhanced raw counts static planar images of sham-operated (left) and infarcted rat (right) acquired at 120 min after the intravenous injection of $^{99m}$Tc-HYNIC-Duramycin, whereby the infarct site is marked by arrows, whereby, in autoradiography, the radioactivity uptake in the myocardium co-localizes with the infarct with excellent infarct-to-noninfarct-ratio (inset), and, whereby the positions of the kidneys and the bladder are marked by "K" and "B", respectively.

FIG. 4: Panel A shows a typical anterior planar images acquired at the same time points after $^{99m}$Tc-Duramycin injection, and, Panel B shows the uptake kinetics of $^{99m}$Tc-HYNIC-Duramycin in the infarcted (stripe), ischemic non-infarct (dotted) and normal (solid) myocardium in a rat model of myocardial ischemia and reperfusion, whereby $^{99m}$Tc-HYNIC-Duramycin was injected 2 hours after injection, whereby radioactivity uptake was sampled at 3, 10, 20, 60 and 180 min post injection, and, whereby each data point represents the mean and standard deviation of measurements from 4 rats.

FIG. 5 shows the characterization of the window of detection for AMI using $^{99m}$Tc-HYNIC-Duramycin in a rat model of myocardial ischemia and reperfusion, whereby Panel A demonstrates typical anterior whole-body planar images acquired at 1 hr after $^{99m}$Tc-HYNIC-Duramycin in rats that were at 2 hr, 1d, 2d, 3d, 5d and 7d post-infarction, whereby the site of the infarction is marked by an arrow, whereby Panel B includes autoradiographs of the short-axial mid-sections of the rat hearts, and, whereby the changes in terms of infarct-to-noninfarct ratios measured from the autoradiographs are plotted in Panel C as a function of age of the infarct.

Figure 8:
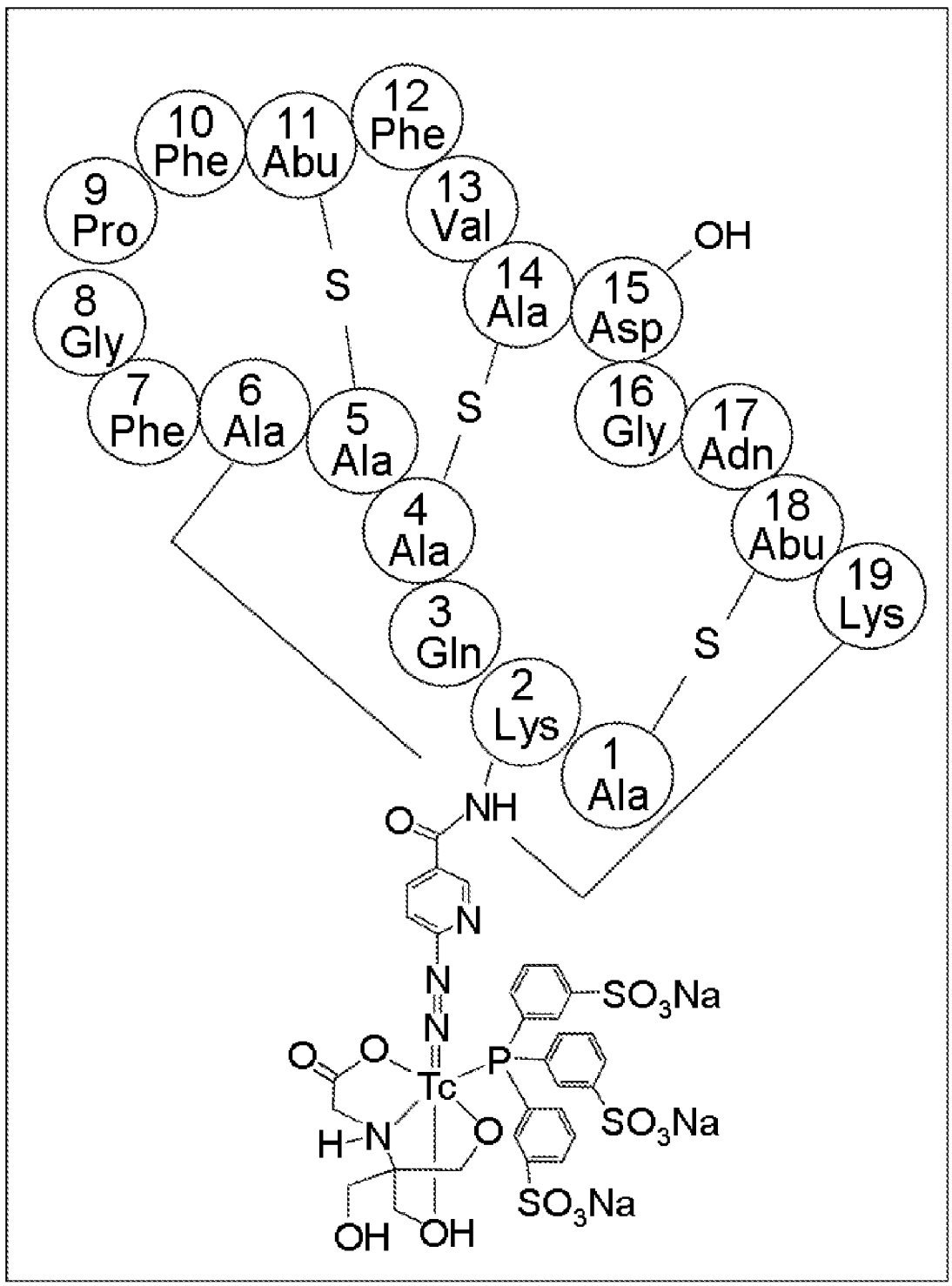

FIG. 8 shows one possible structure for $^{99m}$Tc-HYNIC-Duramycin, whereby other chelation structures may be possible. The instant invention for $^{99m}$Tc-HYNIC-Duramycin is not limited to the structure disclosed in FIG. 8. The structure shown in FIG. 8 is also referred to as $^{99m}$Tc-HYNIC-Duramycin herein.

DETAILED DESCRIPTION OF THE EXEMPLARY EMBODIMENTS

A modified version of Duramycin is defined by SEQ ID. NO. 1, whereby Duramycin is covalently modified at Lysine-2 and/or Alanine-1 by 6-hydrazinopyridine-3-carboxylic acid (HYNIC), thus providing a chelation site for $^{99m}$Tc. (See FIG. 1A-C).

A homologue of Duramycin comprises conservative substitutions at least one amino acid of the polypeptide sequence covalently modified at amino acids located at positions 1 and/or 2 by HYNIC.

Technetium-99m is a metastable nuclear isomer of technetium-99 and is symbolized as $^{99m}$Tc. The "m" indicates that it is a metastable nuclear isomer, which means that it does not change into another element (i.e., transmutate) upon a decay. It is a gamma ray emitting isotope used in radioactive isotope medical tests, for example as a radioactive tracer that medical equipment can detect in the body. It is well suited to the role because it emits readily detectable 140 keV gamma rays (these are about the same wavelength emitted by conventional X-ray diagnostic equipment), and its half-life for gamma emission is 6.01 hours (meaning that about fifteen sixteenths (93.7%) of it decays to $^{99}$Tc in 24 hours). The short half life of the isotope allows for scanning procedures which collect data rapidly, but keep total patient radiation exposure low.

Chelation is the binding or complexation of a bi- or multi-dentate ligand. These ligands, which are often organic compounds, are called chelants, chelators, chelating agents or sequestering agent. Chelants, according to ASTM-A-380, are "chemicals that form soluble, complex molecules with certain metal ions, inactivating the ions so that they cannot normally react with other elements or ions to produce precipitates or scale." The ligand forms a chelate complex with the substrate. The term is reserved for complexes in which the metal ion is bound to two or more atoms of the chelant.

All technical and scientific terms used herein have the same meaning as is commonly understood by one of ordinary skill in the relevant art.

"Active" and/or "activity" means one or more polypeptide forms that retain the biological activity of native Duramycin, whereby activity retention refers to a compound capable of exhibiting substantially similar in vivo activity as the Duramycin polypeptide encoded by SEQ ID. NO. 1.

"Biologically active" means a protein having structural, regulatory, or biochemical functions of a naturally occurring molecule.

"Amino acid" embraces all compounds (natural and synthetic) including both amino functionality and acid functionality, including amino acid analogs and derivatives. The instant amino acids may be those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

"Amino acid residue" means an amino acid or peptide molecule absent the —OH of the carboxyl group. The terminology used herein for designating the amino acids and the protective groups are consistent with the recommendations of the IUPAC-IUB Commission on Biochemical Nomenclature. (*Biochemistry* (1972) 11:1726-1732). For instance Met, Ile, Leu, Ala and Gly represent residues of methionine, isoleucine, leucine, alanine and glycine, respectively, wherein the residue is a radical derived from the corresponding alpha.-amino acid by elimination of the OH from the carboxyl group and the H portion of the alpha.-amino group.

"Apoptosis" means programmed cell death; an endogenous cell death program results in the death of the cell.

"Binding affinity" means a thermodynamic expression of the strength of interaction between a single binding site and a single determinant (and thus of the stereochemical compatibility between them).

"Binding site," means a region of a molecule or molecular complex that (as a result of its shape) favorably associates with (or, binds with) another molecule. Such other molecule being a ligand of the binding site. A binding site, such as that defined by amino acids located in the positions 5-15 of Duramycin, is analogous to a wall and circumscribes a space referred to as a "pocket." The ligand of the binding site situates in the pocket.

"Binding specificity", "specific binding" and "specifically binding" mean interaction between a protein/peptide and an agonist, antibody, antagonist, small molecule or any natural or synthetic binding composition. The interaction is dependent upon the presence of a particular structure of the protein, e.g., the antigenic determinant or epitope, recognized by the binding molecule. For example, the binding pocket of Duramycin resembles a glove-shaped surface that fits around the PtdE head group with well-defined physicochemical interactions. The hydrophobic binding pocket contains lipophilic side chains from Gly-8, Pro-9 and Val-13. The binding of the ethanolamine head group is stabilized by an ionic interaction pair between the ammonium group of PtdE and the carboxylate of Asp-15. The overall tight fitting between the Duramycin binding pocket and the ethanolamine head group confers thermodynamic stability and an exclusive specificity for PtdE.

"Binds" in all its grammatical forms means a condition of proximity between or amongst molecules, chemical compounds or chemical entities. The association may be non-covalent (i.e. non-bonded or reversible), wherein the juxtaposition is energetically favored by hydrogen bonding or van der Waals or electrostatic interactions, or it may be covalent (i.e. bonded or irreversible).

"Chelating agent" means a molecule, often an organic one, having two or more unshared electron pairs available for donation to a metal ion, whereby such complexes involving the bound metal ion includes two or more atoms of the chelant.

"Complex" means a compound formed by the union of one or more electron-rich and electron-poor molecules or atoms capable of independent existence with one or more electronically poor molecules or atoms, each of which is also capable of independent existence.

"Conserved sequence" means similar or identical sequences of nucleic acids or amino acids to multiple other species of organisms, or to different molecules produced by the same organism.

"Conservative amino acid substitutions" means substitutions predicted to least interfere with the properties of the original protein, i.e., the structure and especially the function of the protein is conserved and not significantly changed by such substitutions. Conservative amino acid substitutions generally maintain (a) the structure of the polypeptide backbone in the area of the substitution, (b) the charge or hydrophobicity of the molecule at the site of the substitution, and/or (c) the bulk of the side chain. The invention encompasses substitution of amino acids based upon the probability of an amino acid substitution resulting in conservation of function.

"Elongated" refers to lengthening a peptide or polypeptide, often by sequential addition to either the N- or C-terminus "Functional group" refers to specific groups of atoms within molecules responsible for the characteristic chemical reactions of those molecules. The same functional group will undergo the same or similar chemical reaction(s) regardless of the size of the molecule it is a part of. However, its relative reactivity can be modified by nearby functional groups.

"Homologous," "homolog" or "homologue" means amino acid sequences that share at least 30-40%, 40-50%, 50-60%, 60-70%, 70-80%, 80-90% or 95+% homology and a common functional activity. For example, Cinnamycin is a homolog of Duramycin that has a single amino acid substitution located at position two where Arg replaces Lys. Eighteen of 19 amino acids share the same sequence in Duramycin and Cinnamycin, making their sequence similarity 95%.

"Hydrophobic" means a physical property of a molecule that is repelled from a mass of water. Hydrophobic molecules tend to be non-polar and thus prefer other neutral molecules and non-polar solvents.

"Isotope" means any of the different types of atoms of the same chemical element, each having a different atomic mass, due to different numbers of neutrons.

"Liposome" means a small vesicle composed of various types of lipids, phospholipids and/or surfactant which is useful for delivery of a drug (or a compound such as the one described herein) to a mammal. The components of the liposome are commonly arranged in a bilayer formation, similar to the lipid arrangement of biological membranes.

"Modification" means changes that can occur anywhere in a polypeptide, including the peptide backbone, the amino acid side-chains and the amino or carboxyl termini. A given polypeptide may contain many types of modifications. For example, in the instant invention Duramycin is modified by covalent attachment of HYNIC.

"Moiety" means a specific segment or functional group of a molecule. Chemical moieties are often recognized chemical entities embedded in or appended to a molecule.

"Necrosis" means premature or unnatural death of cells and living tissue caused by external factors, such as infection, toxins, or trauma.

"Nuclide" means an atomic nucleus with a specific number of protons and neutrons. Collectively, all the isotopes of all the elements form the set of nuclides.

"Peptide" and "polypeptide" are used interchangeably and mean a polymer of amino acids. A "polypeptide" is a polymer of amino acid residues joined by peptide bonds, whether produced naturally or synthetically. Polypeptides of less than about 10 amino acid residues are commonly referred to as "peptides."

"Phospholipid" means a class of lipids that form a major component of all cell membranes, whereby they form lipid bilayers. Phospholipids may contain a diglyceride, a phosphate group, and a simple organic molecule.

"Polymer" means a large molecule (macromolecule) comprising repeating structural units typically connected by covalent chemical bonds.

"Protein" means a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins include amino acid backbone structures as well as substituents such as carbohydrate groups generally not specified but present nonetheless.

"Radioisotope" or "radionuclide" mean atoms having an unstable nucleus (characterized by excess energy) available to be imparted to a newly-created radiation particle within the nucleus. The radioisotope undergoes radioactive decay emitting gamma rays.

"Substantial sequence similarity" in the amino acid sequence comparison context means either that the segments (or, their complementary strands) when compared, are identical when optimally aligned with appropriate amino acid insertions, deletions or substitutions in at least about 50% of the amino acids, at least 56%, at least 59%, at least 62%, at least 65%, at least 68%, at least 71%, at least 74%, at least 77%, at least 80%, at least about 85%, at least about 90%, at least about 95 to 98%, or, as high at about 99% or more of the amino acids.

"Substitution" or "substituted with" means implicitly that the substitution results in a stable compound being a compound that does not spontaneously undergo transformation. For example, some kinetic forms are stable.

"Truncated" refers to shortening a peptide or polypeptide, often by cutting the polypeptide short of its native N- or C-terminus. Truncated proteins contemplated by the invention include those having one or more amino acid residues deleted from the carboxy terminus of the peptide, or one or more amino acid residues deleted from the amino terminus of the peptide, or one or more amino acid residues deleted from an internal region (i.e., not from either terminus) of the peptide.

Among acute coronary syndrome (ACS) cases, the ones with atypical symptoms pose a significant challenge in emergency medicine. (Pope J H et al, HP. Missed diagnoses of acute cardiac ischemia in the emergency department, *N Engl J Med* 2000; 342:1163-70; Braunwald E et al, American College of Cardiology, American Heart Association, Committee on the Management of Patients With Unstable Angina, ACC/AHA 2002 guideline update for the management of patients with unstable angina and non-ST-segment elevation myocardial infarction—summary article: a report of the American College of Cardiology/American Heart Association task force on practice guidelines, Committee on the Management of Patients With Unstable Angina, *J Am Coll Cardiol* 2002; 40:1366-74). An imaging technique that can expedite, with specificity, the diagnosis of equivocal ACS cases could also potentially facilitate the management of chest pain patients and provide further insight in understanding heart diseases. Preliminary studies have demonstrated the unique imaging properties of $^{99m}$Tc-Duramycin, which could potentially meet the criteria for diagnostic cardiac imaging. (Zhao M et al., $^{99m}$Tc-labeled Duramycin as a novel hosphatidylethanolamine-binding molecular probe, *J Nucl Med* 2008; 49:1345-52).

As a molecular target for apoptosis imaging, phosphatidylethanolamine (PtdE) is the second most abundant phospholipid, and it accounts for approximately 20% of all phospholipids in mammalian cellular membranes. (Alberts B et al, Molecular biology of the cell, Fourth edition, Garland Science, New York, 2002; Spector A A, Yorek M A, Membrane lipid composition and cellular function, *J Lipid Res,* 1985, 26(9):1015-1035). Like phosphatidylserine (PtdS), PtdE is a constituent of the inner leaflet of the plasma membrane with little presence on the surface of normal viable cells. (Bevers et al., August 1999, *Biochim Biophys Acta.,* 18; 1439(3):317-330). In apoptosis, PtdE is exposed onto the cell surface as the redistribution of phospholipids across the bilayer is facilitated. (Emoto et al., May 1997, *Exp Cell Res* 1; 232(2):430-434). In necrosis, PtdE becomes accessible to the extracellular milieu due to compromised plasma membrane integrity.

In contrast to PtdS (which when externalized serves as a signaling mechanism for the scavenging of the dying cells), the presence of PtdE on the apoptotic cell surface appears to play regulatory roles. Blebbing and the formation of apoptotic bodies are essential processes where intracellular components are discretely packaged and designated for engulfment by scavenger cells without causing inflammation. As one of the morphological hallmarks of apoptosis, blebbing is the consequence of profound membrane structural remodeling. It has been demonstrated that the trans-bilayer movement of PtdE is especially enhanced on the blebs of apoptotic cells, and, the morphological changes are in part attributed to the PtdE-mediated reorganization of actin filaments. (Umeda M et al, Membrane phospholipid dynamics during cytokinesis: regulation of actin filament assembly by redistribution of membrane surface phospholipid, *Chem Phys Lipids,* 1999, 101(1):81-91; Mills J C et al, Apoptotic membrane blebbing is regulated by myosin light chain phosphorylation, *J Cell Biol,* 1998, 140(3):627-636).

A molecular probe candidate for PtdE is Duramycin, a 19-amino acid peptide produced by *Streptoverticillium cinnamoneus.* (Hayashi F et al, The structure of PA48009: the revised structure of Duramycin, *J Antiboiot* (Tokyo), 1990, 43(11):1421-1430; Zimmermann N et al, Solution structures of the lantibiotics Duramycin B and C, *Eur J Biochem,* 1993, 216(2):419-428). Duramycin binds the head group of PtdE with high affinity at a molar ratio of 1:1. (Marki F et al, Mode of action of the lanthionine-containing peptide antibiotics Duramycin, Duramycin B and C, and Cinnamycin as indirect inhibitors of phospholipase A2, *Biochem Pharmacol.,* 1991, 42(10):2027-2035; Iwamoto K et al., Curvature-dependent recognition of ethanolamine phospholipids by Duramycin and Cinnamycin, *Biophys J.* 2007, 93(5):1608-1619; Seelig J, Thermodynamics of lipid-peptide interactions, *Biochim Biophys Acta.,* 2004, 1666(1-2):40-50).

The overall structure of Duramycin assumes a compact cyclic configuration with a single binding pocket that specifically interacts with PtdE. (Hayashi 1990; Zimmerman 1993). Stabilized by three internal thioether linkages, Duramycin is the smallest known polypeptide that has a defined 3-dimensional binding site. (Hayashi 1990; Zimmerman 1993). The binding pocket of Duramycin resembles a glove-shaped surface that fits around the PtdE head group with well-defined physicochemical interactions. The hydrophobic binding pocket contains lipophilic side chains from Gly-8, Pro-9 and Val-13. The binding of the ethanolamine head group is stabilized by an ionic interaction pair between the ammonium group of PtdE and the carboxylate of Asp-15. The overall tight fitting between the Duramycin binding pocket and the ethanolamine head group confers thermodynamic stability and an exclusive specificity for PtdE. In addition, two Phe side chains protrude from the upper loop stabilize the Duramycin-membrane binding by anchoring to the hydrophobic core of the membrane bilayer.

The biological activities of Duramycin and its close analog, Cinnamycin, have been well-characterized, and their PtdE-binding activity have been exploited for in vitro biological studies. (Aoki Y et al., A novel peptide probe for studying the transbilayer movement of phosphatidylethanolamine, *J Biochem* (Tokyo), 1994, 116(2):291-297; Machaidze G et al., Specific binding of Ro 09-0198 (cinnamycin) to phosphatidylethanolamine: a thermodynamic analysis, *Biochemistry,* 2002, 41(6):1965-1971; Guder A et al., Posttranslationally modified bacteriocins—the lantibiotics, *Biopolymers,* 2000, 55(1):62-73; Hosoda K et al., Structure determination of an immunopotentiator peptide, cinnamycin, complexed with lysophosphatidylethanolamine by 1H-NMR1, *J Biochem* (Tokyo), 1996, 119(2):226-230; Kaletta C et al., Prepeptide sequence of cinnamycin (Ro 09-0198): the first structural gene of a Duramycin-type lantibiotic, *Eur J Biochem,* 1991, 199(2):411-415).

Duramycin and Cinnamycin have similar PtdE-binding activities, whereby the two peptides differ by a single amino acid at the distal end away from the binding pocket. Using liposomes, it was demonstrated that these peptides bind PtdE at equal-molar ratio with a dissociation constant in the nanomolar range. (Guder 2000; Hosoda 1996; Kaletta 1991). With fluorescent labeling, Cinnamycin has been shown to bind to externalized PtdE of apoptotic cells. (Emoto 1997). The invention provides using Duramycin and Cinnamycin peptides, or homologous peptides, to develop molecular probes for in vivo applications due at least in part to their low molecular weight, high stability, high binding affinity and specificity to PtdE. Similarity between Duramycin and Cinnamycin is also reflected by their amino acid sequences (Table 1).

TABLE 1

| Polypeptide | Amino Acid Sequence | SEQ. ID. NO. |
|---|---|---|
| Duramycin | CKQSCSFGPFTFVCDGNTK | 1 |
| Cinnamycin | CRQSCSFGPFTFVCDGNTK | 2 |
| DuramycinB | CRQSCSFGPLTFVCDGNTK | 3 |
| DuramycinC | CANSCSYGPLTWSCDGNTK | 4 |

It is contemplated here that homologs of Duramycin that retain functional activity of the peptide may also be used in the instant invention. Examples of conserved amino acid substitutions in the binding pocket that are predicted to allow a Duramycin homolog to retain substantial activity are outlined in Table 2. Furthermore, Duramycin, Cinnamycin, and Duramycin homologs may be modified with various functional groups, polymers, peptides, proteins, complexes, particles, or liposomes, without substantially affecting the polypeptide's binding affinity and specificity towards PtdE.

TABLE 2

| Amino Acid Position | Amino Acid Reside | Permissible substitution |
|---|---|---|
| 1 | Cys | |
| 2 | Lys | |
| 3 | Gln | |
| 4 | Ser | |
| 5 | Cys | |
| 6 | Ser | |
| 7 | Phe | Hydrophobic residue |
| 8 | Gly | Hydrophobic residue (not Trp) |
| 9 | Pro | |
| 10 | Phe | Hydrophobic residue |
| 11 | Thr | |
| 12 | Phe | Hydrophobic residue |
| 13 | Val | Hydrophobic residue |
| 14 | Cys | |
| 15 | Asp | |
| 16 | Gly | |
| 17 | Asn | |
| 18 | Thr | |
| 19 | Lys | |

The instant invention covers the synthesis and characterization of technetium-99m-labeled Duramycin for the non-invasive imaging of PtdE as well as HYNIC-modification of Duramycin and radiolabeling thereof. The invention further includes characterization of $^{99m}$Tc-HYNIC-Duramycin as a PtdE-specific, fast-clearing molecular probe. The prompt and conspicuous imaging of acute cell death is demonstrated herein using an in vivo rat model of myocardial ischemia and reperfusion.

$^{99m}$Tc-HYNIC-Duramycin is a PtdE-binding radiopharmaceutical that detects apoptosis/necrosis. It differs from existing imaging tracers in several major aspects. With 19 amino acids, Duramycin is one of the smallest possible polypeptides that has a defined 3-dimensional binding structure. (Hayashi 1990; Zimmerman 1993; Seelig 2004). Duramycin also has antibody-like binding activities as well as small-molecule-like pharmacokinetics. Duramycin further provides rapid renal clearance and a low general (including hepatic) background. (Zhao 2008). Duramycin also binds dead and dying cells by recognizing exposed PtdE with high affinity and specificity (Zhao 2008), which is in contrast to phosphatidylserine (PS)-binding tracers including Annexin V and the C2A domain of Synaptotagmin I. (Zhao M et al., Non-invasive detection of apoptosis using magnetic resonance imaging and a targeted contrast agent, Nat Med, 2001, 7:1241-44; Jung H I et al., Detection of apoptosis using the C2A domain of synaptotagmin I, Bioconjugate Chem, 2004, 15:983-7; Blankenberg F G et al., In vivo detection and imaging of phosphatidylserine expression during programmed cell death, Proc Natl Acad Sci USA, 1998, 95:6349-54; Ohtsuki K et al., Technetium-99m HYNIC-Annexin V: a potential radiopharmaceutical for the in-vivo detection of apoptosis, Eur J Nucl Med, 1999, 26:1251-58; Petrovsky A et al., Near-infrared fluorescent imaging of tumor apoptosis, Cancer Res, 2003, 63:1936-42; Lahorte C M et al, Apoptosis-detecting radioligands: current state of the art and future perspectives, Eur J Nucl Med, 2004, 31:887-919; Taki J et al, Detection of cardiomyocyte death in a rat model of ischemia and reperfusion using 99mTc-labeled annexin V, J Nucl Med, 2004, 45:1536-41; Zhu X et al., Imaging acute cardiac cell death: temporal and spatial distribution of 99mTc-labeled C2A in the area at risk after myocardial ischemia and reperfusion, J Nucl Med, 2007, 48:1031-6; Hofstra L et al, Visualisation of cell death in vivo in patients with acute myocardial infarction, Lancet, 2000, 356:209-12; and, Thimister P W et al., In vivo detection of cell death in the area at risk in acute myocardial infarction, J Nucl Med, 2003, 44:391-6).

Importantly, the instant $^{99m}$Tc-HYNIC-Duramycin provides renal clearance rather than hepatic retention. Native Duramycin is retained for an extended duration (e.g., many days) in the liver without complete washout. Thus, native Duramycin is highly disadvantageous as an imaging agent due to non-clearance and high hepatic background, which would interfere with diagnosis in the thorax and abdominal regions. (McNulty M J et al., Xenobiotica 2003; 33(2):197-210).

The instant $^{99m}$Tc-HYNIC-Duramycin is an unexpectedly superior diagnostic imaging agent.

The preparation and composition of $^{99m}$Tc-HYNIC-Duramycin is also useful for atherosclerotic plaque and acute myocardial infarct indications and imaging methods. Conventional background information is set forth in U.S. Pat. No. 4,952,393, which discloses imaging agents made from $^{99m}$Tc and glucarate for imaging infarcted tissue.

A significant abundance of PtdE in cellular membranes may lead to greater uptake. (Spector 1985; Bevers 1999; Emoto 1997). Duramycin is also extensively cross-linked by intramolecular covalent bridges, and it exhibits extraordinary in vivo stability. (Zhao 2008; Hayashi 1990; Zimmerman 1993).

The instant invention further involves characterization of the uptake kinetics of $^{99m}$Tc-HYNIC-Duramycin in the area-at-risk after myocardial ischemia and reperfusion as well as determining the window of detection after acute coronary event in the rat model of myocardial ischemia and reperfusion. The invention provides significant insights concerning the interactions between $^{99m}$Tc-HYNIC-Duramycin and the target tissue and provides diagnostic use of $^{99m}$Tc-HYNIC-Duramycin as a molecular probe for the non-invasive imaging of PtdE.

The in vivo stability of $^{99m}$Tc-Duramycin may be attributed to at least the following. In terms of radiochemistry, to preserve the convenience of HYNIC radiochemistry, a phosphine compound is provided as a third co-ligand. (Edwards D S et al., New and versatile ternary ligand system for technetium radiopharmaceuticals: water soluble phosphines and tricine as coligands in labeling a hydrazinonicotinamide-modified cyclic glycoprotein IIb/IIIa receptor antagonist with $^{99m}$Tc, Bioconjug Chem., 1997, 8(2):146-154; Liu S et al., $^{99m}$Tc labeling of highly potent small peptides, Bioconjug Chem., 1997, 8(5):621-636). Tricine alone has been widely used as a co-ligand for HYNIC radiochemistry, whereby two tricine molecules form a well-defined coordination complex with $^{99m}$Tc and the hydrazine group of HYNIC. However, the tricine chelation core is known to be less stable under dilute conditions. (Edwards 1997; Liu 1997; Liu S et al., Labeling a hydrazino nicotinamide-modified cyclic IIb/IIIa receptor antagonist with $^{99m}$Tc using aminocarboxylates as coligands, Bioconjug Chem, 1996, 7(1):63-71; Babich J W et al, Technetium-99m-labeled hydrazino nicotinamide derivatized chemotactic peptide analogs for imaging focal sites of bacterial infection, J Nucl Med, 1993, 34(11):1964-1974; Babich J W, Fischman A J, Effect of "co-ligand" on the biodistribution of $^{99m}$Tc-labeled hydrazino nicotinic acid derivatized chemotactic peptides, Nucl Med Biol, 1995, 22(1):25-30).

By including trisodium triphenylphosphine-3,3',3"-trisulfonate (TPPTS) in the coordination chemistry, $^{99m}$Tc-HYNIC-Duramycin remains stable both in solution and in vivo consistent with the prior findings. (Edwards 1997; Liu 1997). Another key factor contributing to the stability of $^{99m}$Tc-HYNIC-Duramycin involves the structural configuration of Duramycin, whereby the polypeptide is stabilized by three internal thioether bridges. (Hayashi 1990; Zimmerman 1993). The absence of free peptidergic terminus (as a result of the circularization of the polypeptide) also minimizes the possibility of proteolytic degradation by blood-borne proteases and peptidases. (Hayashi 1990; Zimmerman 1993). The combination of a stable radiochemistry and the resistance to proteolytic/metabolic degradation synergistically contributes to the overall stability of $^{99m}$Tc-HYNIC-Duramycin in solution and in vivo. These features are demonstrated by the absence of physicochemical degradation of $^{99m}$Tc-HYNIC-Duramycin after intravenous injection and the recovery of the intact radiopharmaceutical in the urine samples.

The binding affinity of Duramycin with PtdE-containing membranes is between 4.8 to 25.0 nM at concentrations that are relevant to an injection dosage for imaging. (Iwamoto 2007). The site of HYNIC attachment and radiolabeling is at the distal end of Duramycin away from the PtdE binding site, so the radiolabeling process has minimal interference with the interactions between Duramycin and PtdE.

Avid accumulation of $^{99m}$Tc-HYNIC-Duramycin in the region of infarction is theoretically due to high levels of accessible PtdE due to extensive cell death by apoptosis and necrosis. The exact roles and percentages of each mode of cell death after ischemia and reperfusion is controversial. The uptake of $^{99m}$Tc-HYNIC-Duramycin in the infarcted myocardium is likely to reflect an overall degree of cellular injuries, whereby PtdE is available for binding in apoptotic cells due to externalization and in necrotic cells when the integrity of the plasma membrane is compromised. (Kostin S et al., Myocytes die by multiple mechanisms in failing human hearts, *Circ Res,* 2003, 92:715-724; Freude B et al., Cardiomyocyte apoptosis in acute and chronic conditions, *Basic Res Cardiol,* 1998; 93:85-89).

The early and prominent appearance of the hot spot uptake at the infarct region also benefits from the prompt receding background due to a fast blood clearance. That conspicuous infarct detection is attributed to the low uptake in the hepatic area, which is in close vicinity of the heart. Although vascular hyper-permeability is a well known consequence of acute myocardial infarction, the fact that there was no washout after the uptake suggests that passive uptake only plays a minor, if not negligible, role in $^{99m}$Tc-HYNIC-Duramycin binding to the infarcted tissue. The PtdE-dependent uptake of $^{99m}$Tc-HYNIC-Duramycin is evident from the lack of retention in the infarct tissue when Duramycin is inactivated as in the case of $^{99m}$Tc-HYNIC-Duramycin, which is supported by the washout of other non-specific contrast agents from infarct tissues in prior imaging and histology studies. (Kim R J et al., Myocardial Gd-DTPA kinetics determine MRI contrast enhancement and reflect the extent and severity of myocardial injury after acute reperfused infarction, *Circulation,* 1996, 94:3318-3326; Zhu X et al., Assessment of reperfused myocardial infarction in the hyper-acute phase with delayed enhancement magnetic resonance imaging, *J Cardiovasc Magn Reson,* 2006, 8(3):461-467; Zhao M et al., $^{99m}$Tc-labeled C2A domain of synaptotagmin I as a target-specific molecular probe for noninvasive imaging of acute myocardial infarction, *J Nucl Med.* 2006, 47(8):1367-1374).

Phospholipid-binding molecular probes hold promise in the non-invasive detection and quantification of acute cell death taking advantage of the asymmetrical distribution of defined phospholipid species between the plasma membrane bilayer. Among these, the characterization and utilities of Annexin V and the C2A domain of Synaptotagmin I have been reported in various applications. (Zhao 2006; Zhu 2007; Liu Z et al., In vivo dynamic imaging of myocardial cell death using $^{99m}$Tc-labeled C2A domain of Synaptotagmin I in a rat model of ischemia and reperfusion, *Nucl Med Biol,* 2007, 34 (8):907-15; Audi S et al., Quantitative Analysis Of $^{99m}$Tc-C2A-GST Distribution In The Area-At-Risk After Myocardial Ischemia And Reperfusion Using A Compartmental Model, *Nucl Med Biol,* 2007, 34(8):897-905; Zhao 2001; Fang W et al., SPECT Imaging of Myocardial Infarction Using $^{99m}$Tc Labeled C2A Domain of Synaptotagmin I in a Porcine Ischemia Reperfusion Model, *Nucl Med Biol,* 2007, 34(8):917-23; Jung 2004; Krishnan A S et al., Detection of cell death in tumors by using MR imaging and a gadolinium-based targeted contrast agent, *Radiology,* 2008 March, 246 (3):854-62, Epub 2008 Jan. 9; Tait J F et al., Structural requirements for in vivo detection of cell death with $^{99m}$Tc-Annexin V, *J Nucl Med,* 2005, 46(5):807-815; Hofstra 2000; Blankenberg 1998; Ohtsuki 1999; Petrovsky 2003; Lahorte 2004; Sosnovik D E, Schellenberger E A, Nahrendorf M et al., Magnetic resonance imaging of cardiomyocyte apoptosis with a novel magneto-optical nanoparticle, *Magn Reson Med,* 2005 September, 54(3):718-24).

Both Annexin V and C2A are calcium-dependent phospholipid-binding proteins, whereby calcium ions in the binding pocket mediate the binding between the protein and the lipid membrane in the form of calcium bridges. (Huber R et al., The crystal and molecular structure of human annexin V, an anticoagulant protein that binds to calcium and membranes, *EMBO J,* 1990, 9:3867-3874; Sutton R B et al., Structure of the first C2 domain of synaptotagmin I: a novel Ca2+/phospholipid-binding fold, *Cell,* 1995, 80:929-938). In comparison, the binding between Duramycin and PtdE is calcium-independent and involves multiple interactions of the peptide side chains with the ethanolamine head group and the hydrophobic fatty acid tails. (Hayashi 1990; Zimmerman 1993).

Another important feature of Duramycin is its low molecular weight. At 2 kDa, Duramycin is substantially smaller than Annexin V (32-36 kDa) and C2A (12 kDa). The unexpectedly dramatic enhanced rate of blood clearance of $^{99m}$Tc-HYNIC-Duramycin is consistent with its low molecular weight, which is apparent from the collection of the bulk of the injected dose in the urine.

Although it is possible that PtdE binding may be accompanied by non-specific uptake, none was observed in the instant invention. According to the instant biodistribution data, the uptake of $^{99m}$Tc-HYNIC-Duramycin was low in tissues, including the liver. This was consistent with the in vivo whole-body imaging, whereby $^{99m}$Tc-HYNIC-Duramycin was cleared via the renal-urinary system without significant retention in the body.

Duramycin is produced by *S. cinnamoneus,* whereby immunogenicity may become a concern. However, Duramycin is an antibiotic used to treat certain types of bacterial infections, including those found in patients suffering from Cystic Fibrosis. The lack of significant toxicity and immunogenicity is evident from clinical practice involving Duramycin.

HPLC purification is necessary to obtain the radiotracer at satisfactory radiochemical quality for in vivo imaging. To address that requirement, radiolabeling conditions were optimized by providing a single-step labeling protocol without the need for further purification. The HYNIC derivatized Duramycin (i.e., the radiolabeled compound) is not isomerically homogeneous because there are two primary amines on the surface of Duramycin. Elimination of one of the amines may be performed.

$^{99m}$Tc-labeled Duramycin in combination with the HYNIC-tricine-phosphine chelation core is highly stable in solution and in vivo. The PtdE-binding activity and specificity of $^{99m}$Tc-HYNIC-Duramycin are well-preserved after radiolabeling. The radiopharmaceutical has favorable pharmacokinetic and biodistribution profiles in vivo. Combined with a fast blood clearance and low hepatic uptake, avid binding of $^{99m}$Tc-HYNIC-Duramycin to the site of acute myocardial infarction allows prompt and conspicuous imaging shortly after injection. $^{99m}$Tc-HYNIC-Duramycin provides a superior molecular probe for the non-invasive imaging of PtdE, which has important and significant clinical implications.

The instant invention provides several significant discoveries. $^{99m}$Tc-HYNIC-Duramycin has rapid uptake reaching high levels in infarcted as well as ischemic-non-infarct myocardium. The instant radiotracer is sequestered in the damaged tissues in a PtdE-dependent manner. Once bound, there is little washout over an extended period of time. The instant imaging technique has a reasonably wide window of detection after acute myocardial infarction (AMI), whereby the infarct tissue can be detected for approximately 2 days. As a radiopharmaceutical, $^{99m}$Tc-HYNIC-Duramycin meets a number of important criteria for cardiac imaging applications, which are further discussed below.

The kinetics of $^{99m}$Tc-HYNIC-Duramycin in the area-at-risk exhibits unexpectedly superior higher uptake at a faster rate compared to a macromolecular agent, such as $^{99m}$Tc-C2A-GST. (Zhao 2006; Liu Z. 2007; Audi S et al., Quantitative Analysis Of $^{99m}$Tc-C2A-GST Distribution In The Area-At-Risk After Myocardial Ischemia And Reperfusion Using A Compartmental Model, *Nucl Med Biol*, 2007, 34:897-905). Specifically, the level of $^{99m}$Tc-HYNIC-Duramycin in the area-at-risk approached a plateau of ~4.0% ID/g within 10 minutes after injection. In the same animal model, the uptake of $^{99m}$Tc-C2A-GST reached the plateau of only about 2.5% ID/g in 30 minutes. (Liu 2007; Audi 2007).

Without being bound to any theory, the differences can be attributed to at least two underlying factors that govern the in vivo behaviors of an imaging agent. Quantitative analysis in prior investigations indicates that the rate of diffusion can be a major limiting factor for the uptake of a macromolecular probe. (Audi 2007). Cognate interactions between the probe and the binding target are dependent on the probe's ability to navigate the target tissue. Smaller probes have a greater rate of diffusion and more easily cross the endothelial barrier, which lead to a more efficient target binding. The molecular weights of C2A-GST and Duramycin are 37 and 2 kDa, respectively. The significant difference in molecular size is consistent with the higher and faster uptake of $^{99m}$Tc-HYNIC-Duramycin in the target tissue.

Another factor that may contribute to the higher uptake of $^{99m}$Tc-HYNIC-Duramycin is that in a typical mammalian cell the content of PtdE is several folds greater than PS. (Spector 1985). Duramycin and C2A bind PtdE and PtdS, respectively. While the externalization of the two types of phospholipids is synchronized in dying cells, a higher abundance of binding targets enhances probe uptake. (Bevers 1999; Emoto 1997). Therefore, faster and greater uptake of $^{99m}$Tc-HYNIC-Duramycin in the area-at-risk is likely a reflection on a combination of higher abundance of PtdE and better diffusion of $^{99m}$Tc-HYNIC-Duramycin in the target tissue.

$^{99m}$Tc-HYNIC-Duramycin imaging agents identify cardiac cell death in the acute phase, and, there is an extended imaging window for detection. The data with planar imaging demonstrate such. The window of detection is estimated at ~48 hours post infarction. The data indicate that the presence of PtdE as a molecular marker for cell death persists for a duration after the initial ischemic challenge—either from continuous cell death or as cell debris that are yet to be scavenged. Since PtdE is accessible in both apoptotic and necrotic cells, use of $^{99m}$Tc-HYNIC-Duramycin for imaging detects both forms of cell death in terms of the overall tissue damage. The level of tracer uptake subsides with time, and diminishes toward the baseline at or after 7 days post infarction. $^{99m}$Tc-HYNIC-Duramycin imaging agents detect AMI at the acute stage, and the window of detection is sufficiently broad to capture late cases. As projected into perspective, an extended imaging window assists in diagnosing acute coronary cases where patients fail to seek immediate medical attention.

Blood pool and hepatic background are two of the most important hurdles for existing and potential heart imaging agents. Both elements are in close proximity to the myocardium, and a high background in either one is likely to compromise the image quality. Anti-myosin antibodies (which are relatively large macromolecules) have slow clearance and high hepatic retention that preclude a prompt imaging after intravenous injection. (Khaw B A, The current role of infarct avid imaging, *Semin Nucl Med*, 1999, 29:259-70; Khaw B A et al., Scintigraphic quantification of myocardial necrosis in patients after intravenous injection of myosin-specific antibody, *Circulation*, 1986, 74:501-8; Khaw B A et al., Acute myocardial infarct imaging with indium-111-labeled monoclonal antimyosin, *Fab. J Nucl Med*, 1987, 28:1671-8).

Blood pool and hepatic background are lessened by using mid-sized protein-based agents, including Annexin V and C2A domain of Synaptotagmin I. However, it remains difficult to acquire quality images within several hours after injection in humans and large AMI animal models due to a high cardiovascular blood pool and/or hepatic background. (Hofstra 2000; Thimister 2003; Fang 2007).

In comparison to anti-myosin antibody, annexin V and C2A, $^{99m}$Tc-HYNIC-Duramycin has significantly more favorable pharmacokinetics and biodistribution profiles as evidenced by fast blood clearance and very low hepatic background. (Zhao 2008). The cognate interactions between $^{99m}$Tc-HYNIC-Duramycin and PtdE resembles antibody-antigen interactions. (Hayashi 1990; Zimmerman 1993; Seelig 2004). The in vivo kinetics of $^{99m}$Tc-HYNIC-Duramycin also mirror that of a small hydrophilic molecule. (Zhao 2008). These properties provide synergistic advantages favorable to conspicuous visualization of the infarction in the thorax due to avid target uptake accompanied by fast background clearance.

The data herein provides quantitative accounts regarding the uptake kinetics of $^{99m}$Tc-HYNIC-Duramycin in the area-at-risk in the rat model of re-perfused AMI. The binding of $^{99m}$Tc-HYNIC-Duramycin to damaged myocardium is avid and persists over time without significant washout. $^{99m}$Tc-HYNIC-Duramycin imaging agents detect infarctions at the acute phase, and, they allow an extended imaging window of about 2 days post infarction.

$^{99m}$Tc-HYNIC-Duramycin imaging agents are also useful in heart imaging applications. Given reasonable extrapolations and high target-to-background ratios, $^{99m}$Tc-HYNIC-Duramycin imaging agents are useful for assessing tissue transplantation rejection, monitoring of cancer treatment, and, other degenerative pathologies involving acute cell death.

As used herein, "salts" of the instant compound may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those disclosed in Berge S M et al., "Pharmaceutical Salts." J. Pharm. Sci. 66:1-19 (1977) and Haynes D A et al., "Occurrence of pharmaceutically acceptable anions and cations in the Cambridge Structural Database," J. Pharm. Sci. 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, and triethiodide.

As used herein, "hydrates" of the instant compound may be a pharmaceutically suitable (i.e., pharmaceutically acceptable) hydrate that is a compound formed by the addition of water or its elements to a host molecule (e.g., the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Solvates and hydrates may also be referred to as "analogues."

As used herein, the injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

EXAMPLES

HPLC method 1. Jupiter $C_{18}$ column (90 Å pore size, 250×4.6 mm, Phenomenex) was used with a mobile phase system consisting of acetonitrile and water at a flow rate of 1.0 ml/min at room temperature. A baseline of 5 min at 90% buffer A (water with 0.1% trifluoroacetic acid, v/v) and 10% buffer B (acetonitrile with 0.1% trifluoroacetic acid, v/v) was followed by a linear gradient to 10% buffer A and 90% buffer B in 35 min.

HPLC method 2. Jupiter $C_{18}$ column (90 Å pore size, 250×4.6 mm) was used with a buffered mobile phase system consisting of phosphate buffer (10 mM sodium phosphate, pH 6.7) and acetonitrile at a flow rate of 1.0 ml/min at room temperature. A baseline of 5 min at 90% buffer A (phosphate buffer, pH6.7) and 10% buffer B (acetonitrile) was followed by a linear gradient to 10% buffer A and 90% buffer B in 30 min. The level of radioactivity in the HPLC elute was monitored by gamma counting at an energy window of 140±15 keV.

Radiolabeling of Duramycin. Duramycin was labeled with $^{99m}$Tc after HYNIC modification. Specifically, the HYNIC-conjugated Duramycin was synthesized by reacting succinimidyl 6-hydrazinonicotinate acetone hydrazone with Duramycin at a molar ratio of 8:1, in the presence of 4 equivalents of triethylamine. The reaction was carried out in dimethylformamide (DMF) for 18 hrs at room temperature with gentle stirring. HYNIC-Duramycin was purified using HPLC method 1. The fractions that contained HYNIC-Duramycin were pooled, aliquoted into 15 µg fractions, freeze-dried and stored under argon at −80° C. until use. The molecular weight of the final product was confirmed using matrix-assisted laser desorption/ionization (MALDI) mass spectrometry. The use of HYNIC to prepare $^{99m}$Tc-labeled polypeptides has been reported. (Ono M et al., (99m)Tc-HYNIC-derivatized ternary ligand complexes for (99m)Tc-labeled polypeptides with low in vivo protein binding, *Nucl Med Biol. April* 2001, 28(3):

215-24; Zhao M et al., $^{99m}$Tc-Labeled Duramycin as a Novel Phosphatidylethanolamine-Binding Molecular Probe, *J Nucl Med* 2008, 49:1345-1352).

To synthesize a control peptide which does not bind PtdE but has minimally altered structure and molecular weight of Duramycin, Duramycin was inactivated by modifying a carboxylate group of Asp-15 in the binding pocket. The blocking reaction was carried out in DMF at room temperature, with Duramycin, ethanolamine and N-(3-dimethylaminopropyl)-N-ethylcarbodiimide hydrochloride at a molar ration of 1:10:40. The inactivated compound, Duramycin$^I$, which is used herein as a control, was purified by $C_{18}$ reversed phase HPLC. For radiolabeling, Duramycin$^I$ was derivatized with HYNIC, purified by $C_{18}$ reversed phase HPLC and aliquoted as described herein.

HYNIC-Duramycin was labeled with $^{99m}$Tc using the tricine-phosphine co-ligand system. Specifically, 15 μg of HYNIC-Duramycin was mixed with 40 mg of tricine, 1 mg of TPPTS and 20 μg SnCl$_2$ in 0.8 ml at pH 5.3. The labeling was initiated with the addition of about 1 mCi of $^{99m}$Tc. The incubation was allowed to proceed for 40 min at room temperature. The final radiopharmaceutical, $^{99m}$Tc-HYNIC-Duramycin, was analyzed and purified using HPLC method 2. After purification, acetonitrile was removed by evaporation under nitrogen, and $^{99m}$Tc-HYNIC-Duramycin was reconstituted in saline for usage. $^{99m}$Tc-HYNIC-Duramycin$^I$ was synthesized in the same fashion. For stability tests, cysteine challenge was carried out at a cysteine-to-$^{99m}$Tc-Duramycin ratio of 100 to 1, in 0.01 mM phosphate buffer (pH 6.8) for 2 hr at room temperature. The sample was analyzed with radio-HPLC (method 2).

Preparation of Liposomes. Liposomes with the Following Chemical compositions were made: PtdC (100%), PtdC/PtdE (50/50, w/w), PtdC/PtdS (50/50, w/w), PtdC/PtdG (50/50, w/w). Solid phospholipids were weighed to contain 2 mg for each type of lipids in separate glass test tubes (10×140 mm). One ml of chloroform was used to completely dissolve the phospholipid in each tube. The chloroform was evaporated under a stream of nitrogen where the dried phospholipids formed a thin film of residue on the test tube wall. The samples were thoroughly dried under vacuum overnight. The next morning each sample was re-suspended in 2 ml of HEPES buffer (15 mM HEPES, 120 mM NaCl, pH 7.4) at 45° C. Each suspension was sonicated for 2-5 min at 15 sec each cycle until the mixture turned into an opaque appearance, which indicated the formation of multi-laminar liposomes. The samples were kept on ice until use.

In vitro binding tests. The PtdE-binding activity of $^{99m}$Tc-HYNIC-Duramycin was examined using binding assays in vitro. A good source of exposed PtdE was apoptotic Jurkat lymphocytes incubated with 5 μM final concentration of camptothecin at 37° C. in a humidified atmosphere with 5% CO$_2$. Untreated control or treated cells were harvested by centrifugation at 800 g for 5 min and re-suspended at 2×10$^6$ per ml. Radiolabeled Duramycin or Duramycin$^I$ (inactivated Duramycin) was added to each ml of cells at a final concentration of 100 nM, and the binding was allowed to proceed for 5 min at room temperature. The mixture was then loaded onto a layer of Histopaque. After centrifugation at 800 g for 5 min, cell pellet was collected at the bottom of the tube below the Histopaque layer, whereas the media that contained the non-bound radioactivity will remain above Histopaque. The aqueous supernatant was removed by gentle aspiration. The tip of the tube that contains the pellet was cut off using a hot scalpel. Bound radioactivity was determined by direct gamma counting at an energy window of 140±15 keV.

Competition assay. The retention of the binding activity was determined using a competition assay in the presence of PtdE-containing liposomes. PtdC/PtdE liposomes was prepared as described herein. Binding assay was carried out in triplicate in the presence of increasing amount of PtdC/PtdE liposomes, from 1 nM to 10 μM final concentration in 4-fold increments. The radioactivity bound to the cell pellet was determined by gamma counting as described in the precious paragraph. The assay was repeated using liposomes containing other species of closely related phospholipids, including PtdC, PtdG, and PtdS.

Blood half-life and pharmacokinetic studies. The animal protocol used was approved by the Institutional Animal Care and Use Committee under the NIH guideline. Healthy Sprague Dawley rats were injected with radiolabeled Duramycin (2.3 nmole) via the tail vein. At each designated time point, including 0, 1, 5, 15, 30, and 60 min, 50 μl of blood was withdrawn from a pre-installed femoral artery catheter and collected in heparinized tubes. The blood sample was centrifuged at 5000 g, and the radioactivity in the cellular and plasma fractions was measured separately by direct gamma counting using an energy window of 140±15 keV. The data output included total blood activity with time, and the activity associated with blood cells and the plasma, respectively. The blood half-life measurement was conducted in triplets. To analyze the pharmacokinetics of the radiopharmaceutical, 10 μl of the plasma or urine sample was analyzed using HPLC method 2 which involves the physical separation of molecules based upon the matrix-solvent interactions.

Biodistribution studies. Healthy Sprague Dawley rats were injected with radiolabeled Duramycin (2.3 nmole). Dynamic whole-body biodistribution profile was acquired using an in-house gamma camera (GE XRT). The anesthetized animal was continuously imaged at an energy window of 140±15 keV, field of view 22.5×22.5 cm, matrix 128×128, at 1 min per image for up to 60 min post-injection.

For quantitative biodistribution, at each designated time point after intravenous injection of radiolabeled Duramycin, including 0, 1, 5, 15, 30, and 60 min, a group of 4 rats were sacrificed. Various tissues were dissected, rinsed in saline, weighed, and the level of radioactivity was determined using direct gamma counting (140±15 keV).

In vivo imaging of acute cardiac cell death using a rat model of ischemia and reperfusion. Sprague Dawley rats were anesthetized with sodium pentobarbital (50 mg/kg body weight) intraperitoneally. After tracheotomy and intubation, respiration was maintained using a rodent ventilator. The proximal left anterior descending coronary artery (LAD) was occluded using a 6.0 suture at 1 mm below the left atrial appendage. For sham operation, the suture was only passed underneath the LAD without ligation. The presence of acute ischemia/reperfusion was confirmed by the pale appearance in the area-at-risk region and changes in ECG profiles including immediate elevation of ST segment, significant increase in the QRS complex amplitude and width. The coronary ligation was proceeded for 30 min. After reperfusion the chest wall was closed by suturing in layers and ventilation was maintained until the rat could regain spontaneous respiration.

After 2 hr of reperfusion, $^{99m}$Tc-HYNIC-Duramycin or $^{99m}$Tc-HYNIC-Duramycin$^I$ (2.3 nmole, ~200 μCi) was injected via the tail vein. Dynamic in vivo planar imaging was performed using a gamma camera with an energy window at 140±15 keV, matrix size 128×128, field of view 22.5×22.5 cm, at 5 min per image for 60 min. Static images with 500 k counts were acquired after dynamic imaging.

At the end of the imaging study, the animal was sacrificed. The heart was excised and quickly rinsed in saline. About 2 ml of 0.5% triphenyl tetrazolium chloride (TTC) in HEPES buffer (w/v) was infused retrograde into the aorta to stain the entire myocardium. After 15 min incubation at 37° C., the heart was fixed in 4% formaldehyde. Short axis sections of the heart with a thickness of ~500 μm were cut and exposed to Kodak BMX MS film overnight at −80° C. After the film was developed, each corresponding slice was differentiated overnight in 1% formaldehyde in PBS (v/v). Digitized autoradiography and histology section images were visually inspected. For measuring the radioactivity uptake in the infarcted tissues, the heart was harvested and stained by TTC as described above. Infarcted myocardium was dissected from the viable tissue. After weighing, the radioactivity in the specimen was measured by gamma counting with an energy window at 140±15 keV. The data were converted to % ID/g.

Figure 1:
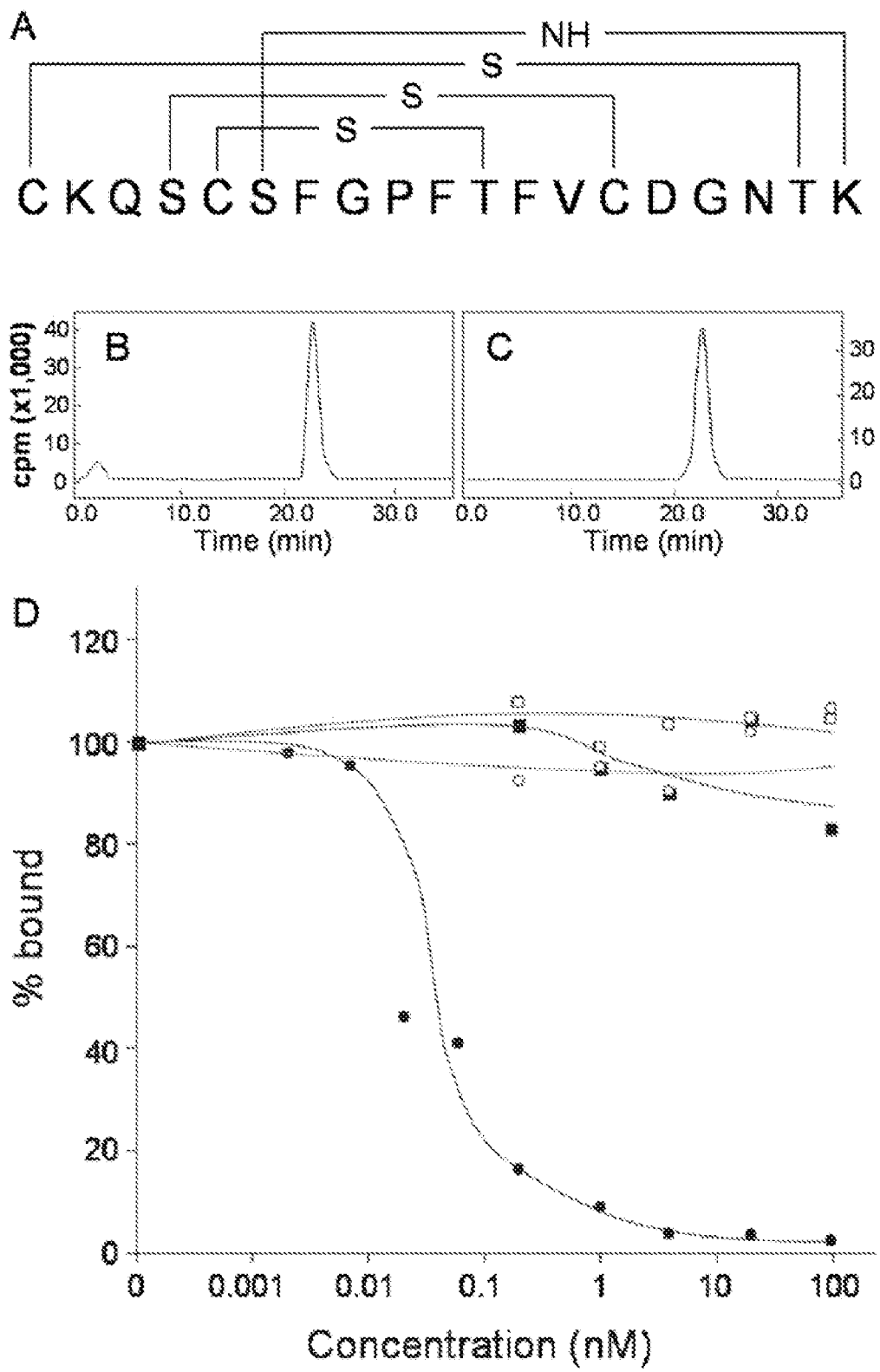

Bioconjuation and radiolabeling. After conjugation, the molecular weight of HYNIC-Duramycin was confirmed using mass spectrometry (expected MW=2188.4 g/mole, actual MW=2188.4 g/mole). At this molecular weight, there is one HYNIC covalently attached to each molecule of Duramycin. The primary sequence of Duramycin has 19 amino acids in the order of CKQSCSFGPFTFVCDGNTK. (Table 1). Two primary amines are available for conjugation at the N-terminal Cys-1 and the side chain of Lys-2. (FIG. 1A). HYNIC-conjugated Duramycin may be in the form of isomers, where the HYNIC moiety is present on either Cys-1 or Lys-2. The Duramycin conjugate with two HYNIC moieties was removed by HPLC purification and confirmed by mass spectra.

FIG. 1B demonstrates a typical radio-chromatogram, where $^{99m}$Tc-HYNIC-Duramycin was eluted with a retention time of 24 min. At the current labeling condition, the labeling efficiency was 80 to 85%, the radiochemical purity was between 78% to 89% before HPLC purification, and the specific activity was $2\times10^5$ Ci/mole. Although column chromatography purification (FIG. 1B and FIG. 1C) is necessary to obtain the final radiopharmaceutical for further experiments, the current radiolabeling protocol is sufficiently amenable to conduct our preliminary studies. Once purified, $^{99m}$Tc-HYNIC-Duramycin is stable, and no significant level of detached $^{99m}$Tc was detected for at least 24 hrs in aqueous solution. This result is consistent with prior reports that phosphine co-ligand substantially improves the stability of $^{99m}$Tc coordination compared to tricine alone. (Edwards 1997; Liu 1997).

When the native form of Duramycin was labeled with $^{99m}$Tc without HYNIC, the radiochemical yield was about 10%. In a cysteine challenge experiment, the radioactivity associated with the native Duramycin was diminished by another 90% at a cysteine-to-Duramycin ratio of 100:1. In contrast, under the same conditions, the radioactivity bound to HYNIC-Duramycin was reduced by less than 3%. These results indicate that the native form of Duramycin could indeed take up limited amount of $^{99m}$Tc, but may only do so loosely without forming well-defined coordination complex. The presence of HYNIC, or another form of chelation core, is essential for the stable labeling of Duramycin with $^{99m}$Tc.

In vitro binding tests. The cellular binding of $^{99m}$Tc-HYNIC-Duramycin was dramatically enhanced in apoptotic versus viable control cells, and the binding was competitively abolished in the presence of PtdE-containing liposomes.

$^{99m}$Tc-HYNIC-Duramycin was incubated with $2\times10^6$ viable Jurkat lymphocytes as control or apoptotic cells induced by camptothecin treatment. While the radioactivity uptake in viable cells remained near background, the binding of $^{99m}$Tc-HYNIC-Duramycin to apoptotic cells was elevated by 32±6 folds (n=3). According to FIG. 1D, such binding to the apoptotic cells was exclusively and competitively diminished in the presence of increasing concentration of PtdE-containing liposomes. Liposomes consisting of PtdC, PtdG or PtdS were also unable to competitively reduce the radioactivity uptake of $^{99m}$Tc-HYNIC-Duramycin in apoptotic cells. $^{99m}$Tc-HYNIC-Duramycin$^I$ bound to apoptotic cells only at background levels, and such binding was not competitively diminished in the presence of PtdE-containing liposomes (data not shown).

Pharmacokinetics and biodistribution of $^{99m}$Tc-HYNIC-Duramycin in rats. After intravenous injection, $^{99m}$Tc-HYNIC-Duramycin exhibited rapid clearance with a blood half-life of less than 4 min as demonstrated in FIG. 2A. Regarding the radioactivity in the blood, greater than 95% was associated with the plasma fraction at all time points, which confirms that $^{99m}$Tc-HYNIC-Duramycin had minimal interactions with normal blood cells. According to radio-HPLC analysis of plasma samples, the majority of the injected radioactivity remained as the parent $^{99m}$Tc-HYNIC-Duramycin. (See FIG. 2C and FIG. 2D). A minor peak was present with a longer retention time (27 min), which appears to be in equilibrium with an unknown blood component. (See FIG. 2C and FIG. 2D). The chemical species of this minor peak was not excreted by the renal function since it was not detected in the urine. RadioHPLC analysis of $^{99m}$Tc-HYNIC-Duramycin in the presence of rat serum albumin did not result in any complex formation between the tracer and albumin. After intravenous injection, $^{99m}$Tc-HYNIC-Duramycin may have associated to a degree with the lipoproteins, which are known to contain PtdE. Importantly, the intravenously injected $^{99m}$Tc-HYNIC-Duramycin showed no sign of metabolic degradation, and it was recovered intact from urine samples where no additional radioactive derivatives or $^{99m}$Tc-pertechnetate were detected. (See FIG. 2E).

Figure 3:
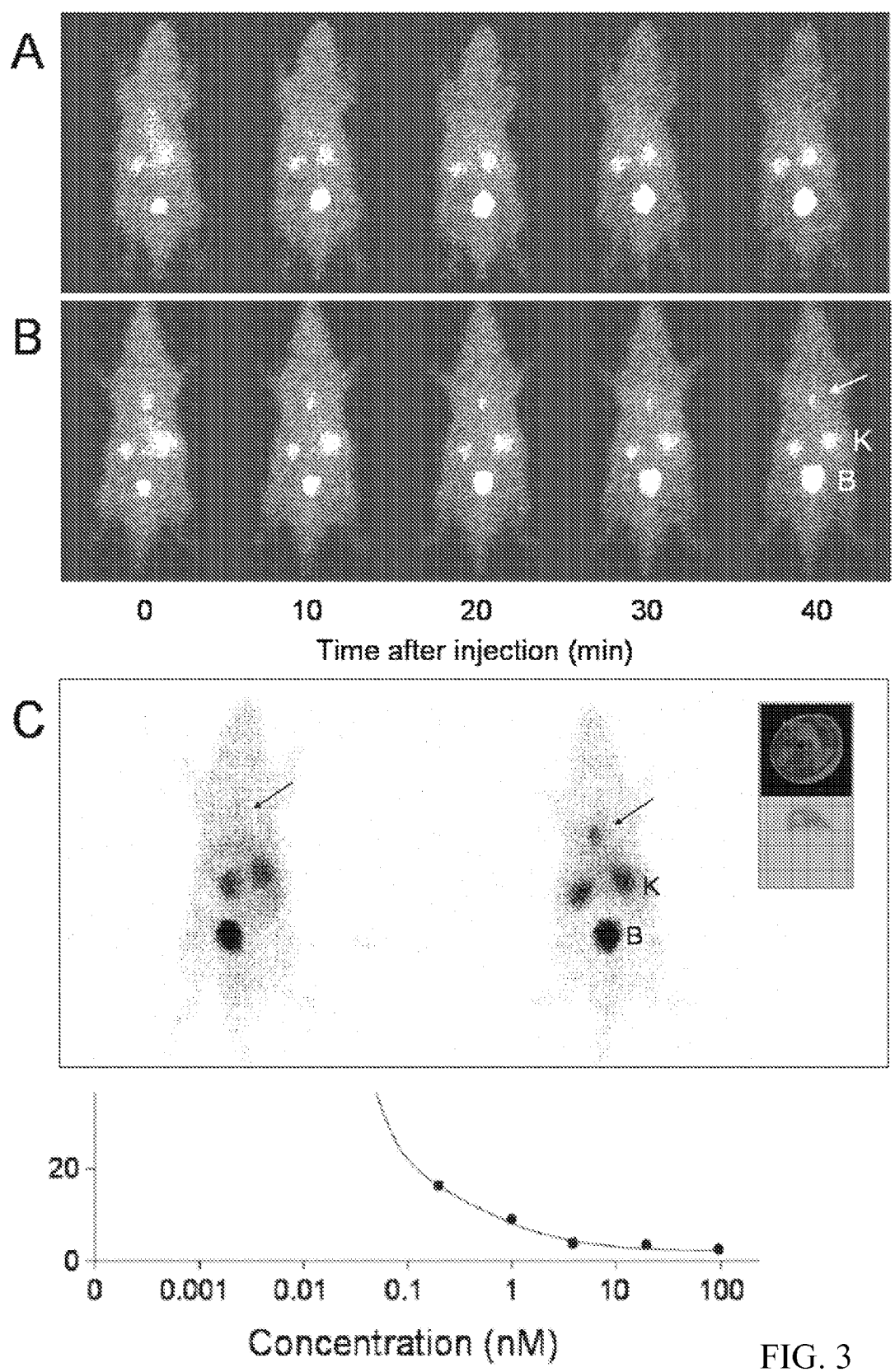

In terms of biodistribution, $^{99m}$Tc-HYNIC-Duramycin renal excretion is the predominant route of clearance with a low uptake in the hepatic and gastrointestinal regions as demonstrated by the data in Table 1. The instant imaging agent does not seem to cross the blood-brain barrier, since the brain uptake was low. (See Table 3, Biodistribution of intravenously injected $^{99m}$Tc-HYNIC-Duramycin in healthy rats at 60 min post-injection (n=4)). The presence of radioactivity in the lungs and the normal myocardium promptly approached background levels with time due to a rapid blood clearance. Thus, an early and clear detection of acute cardiac cell death was achieved as discussed herein. The biodistribution profile was confirmed by in vivo dynamic studies using dynamic anterior planar scintigraphic imaging as shown in FIG. 3A. At the current dosage tested, no signs of toxicity or other adverse effects were observed.

TABLE 3

| Organ/tissue/bodily fluid | Uptake (% ID/g) |
| --- | --- |
| Brain | 0.01 ± 0.01 |
| Thyroid | 0.08 ± 0.03 |
| Lung | 0.12 ± 0.05 |
| Heart | 0.21 ± 0.16 |
| Liver | 0.28 ± 0.01 |
| Pancreas | 0.05 ± 0.01 |
| Spleen | 0.10 ± 0.02 |
| Kidney | 2.32 ± 0.48 |
| Stomach | 0.11 ± 0.01 |
| Small intestine | 0.37 ± 0.07 |
| Colon | 0.11 ± 0.01 |

TABLE 3-continued

| Organ/tissue/bodily fluid | Uptake (% ID/g) |
|---|---|
| Bone | 0.04 ± 0.01 |
| Muscle | 0.03 ± 0.01 |
| Fat | 0.06 ± 0.06 |
| Skin | 0.01 ± 0.01 |
| Blood | 0.33 ± 0.11 |
| Thymus | 0.06 ± 0.02 |
| Urine | 22.1 ± 13.25 |

In vivo imaging of acute cardiac cell death. In dynamic images, a focal uptake was seen at the infarct as early as 10 min after injection (FIG. 3B). The prompt blood clearance and low hepatic uptake facilitated an early and conspicuous appearance of the infarct. At 2 hr after injection, the infarct-to-lung ratio was 4.8±0.4 (n=3), and infarct-to-muscle ratio was 12.2±1.3 (n=3). The distribution of radioactivity in the autoradiography co-localized with the infarct in the histology of the myocardium (FIG. 3C, inset). The level of radioactivity remained persistent with no washout over time. In contrast, the presence of $^{99m}$Tc-HYNIC-Duramycin$^I$ in the infarcted heart was accompanied with a washout, consistent with the lack of PtdE-binding activity. At 1 hr post-injection, the average radioactivity at the infarct site was above 4.0% ID/g for $^{99m}$Tc-HYNIC-Duramycin, whereas that for $^{99m}$Tc-HYNIC-Duramycin$^I$ was less than 1.0% ID/g.

Synthesis of Duramycin and Duramycin$^I$. Duramycin was labeled with $^{99m}$Tc after HYNIC modification using radiochemistry described in the literature. (See Zhao 2008; Edwards 1997; Liu 1997). The HYNIC-conjugated Duramycin was synthesized by reacting succinimidyl 6-hydrazinonicotinate acetone hydrazone with Duramycin in dimethylformamide. HYNIC-Duramycin was purified using C18 reverse phase HPLC (Jupiter $C_{18}$ column, 90 Å pore size, 250×4.6 mm, Phenomenex). To demonstrate the target-specific PE-dependent uptake of the radiotracer, an inactivated form of Duramycin (Duramycin$^I$) was synthesized as described in the literature by chemically converting the carboxyl group at the binding pocket to an ethyl alcohol motif. (Zhao 2008). The modification impairs the interaction between Duramycin and PtdE by compromising the ionic bridge and by partially blocking the binding pocket of Duramycin. Duramycin$^I$ was conjugated to HYNIC and purified using HPLC. The molecular weight of the HYNIC-modified Duramycin and Duramycin$^I$ was confirmed using matrix-assisted laser desorption/ionization (MALDI) mass spectrometry.

Radiolabeling. HYNIC-Duramycin was labeled with $^{99m}$Tc using the tricine-phosphine co-ligand system as reported in Edwards 1997 and Liu 1997. About 10 μg of HYNIC-Duramycin was mixed with 40 mg of tricine, 1 mg of TPPTS and 20 μg $SnCl_2$ in 0.8 ml at pH 5.3. The labeling was initiated by adding about 1 mCi of $^{99m}$Tc. The resultant radiopharmaceutical, $^{99m}$Tc-HYNIC-Duramycin, was purified using HPLC. The level of radioactivity in the HPLC elute was monitored by gamma counting at an energy window of 140±15 keV. After purification, acetonitrile was removed by evaporation under nitrogen, and $^{99m}$Tc-HYNIC-Duramycin was reconstituted in saline for usage. Duramycin$^I$ was radiolabeled in the same fashion.

Acute Myocardial Infarction Model. The animal protocol was approved by the Institutional Animal Care and Use Committee under the NIH guideline. Male Sprague Dawley rats were anesthetized with sodium pentobarbital (50 mg/kg) intraperitoneally. After tracheal intubation, respiration was maintained using a rodent ventilator. An incision was made between the $4^{th}$ inter-costal space to expose the heart. After opening the pericardium, the proximal LAD was occluded for 30 minutes using a 6.0 suture at about 1 mm below the left atrial appendage. For sham operation, the suture was only passed underneath the LAD without ligation. The presence of acute ischemia/reperfusion was confirmed by the pale appearance in the area-at-risk region and changes in electrocardiogram profiles including immediate elevation of ST segment, significant increase in the QRS complex amplitude and width. After reperfusion the chest wall was closed and ventilation was maintained until the rat could regain spontaneous respiration. The loose suture was left in place for area-at-risk staining.

Spatial and Temporal uptake of $^{99m}$Tc-HYNIC-Duramycin in the area-at-risk. To investigate the temporal uptake kinetics of $^{99m}$Tc-HYNIC-Duramycin in the area-at-risk, 20 rats were enrolled to simulate acute myocardial infarction with 30 min coronary occlusion as described above. At 2 hr after reperfusion, the radiotracer was injected intravenously (0.1 mCi). One group of 4 rats was sacrificed for measurements at each of the following time points: 3, 10, 20, 60 and 180 min after injection. Immediately before sacrifice, a second thoracotomy was performed to expose the heart. The LAD was re-occluded at the same location by tightening the suture in place. Two mls of Evans Blue dye (2% w/v in PBS, pH 7.4) was infused into the tail vein. Area-at-risk was delineated by an absence of blue dye uptake, while the normally perfused myocardium is stained dark blue. The heart was quickly excised, and the cardiac tissues from the area-at-risk were dissected and submerged in 0.5% TTC for 15 min at 37° C. Under this staining protocol, the ischemic non-infarct myocardium is stained brick red by TTC, whereas the infarcted tissues are pale. The dissected tissues were separately weighed and collected in sample tubes for gamma counting as follows: normal myocardium (blue), ischemic but viable (red), and infarct (pale). Three aliquots of $^{99m}$Tc-HYNIC-Duramycin solution were taken at 5 μl each and were measured for radioactivity as standards for the calculation of total injected dosage (ID). The radioactivity uptake of $^{99m}$Tc-HYNIC-Duramycin at each time point after injection was presented as percentage of injected dosage per gram (% ID/g) with standard deviation.

Window of detection. To determine the window of detection for AMI using $^{99m}$Tc-HYNIC-Duramycin, the uptake of the radiotracer was examined at different time points after reperfusion. Specifically, 24 rats were enrolled to simulate different durations of reperfusion after 30 min coronary occlusion. $^{99m}$Tc-HYNIC-Duramycin was injected intravenously (0.1 mCi) at 0.1, 1, 2, 3, 5 and 7 days after reperfusion. At each time point, planar imaging was acquired on a group of 4 rats. An anterior planar image of each rat (prone position) was acquired at 60 min after radiotracer injection on a GE XRT γ-camera (GE Healthcare, Waukesha, Wis.) equipped with a high-resolution parallel-hole collimator, with a 15% energy window centering at 140 keV. The field of view was 22.5×22.5 mm with 512×512 matrix.

To validate the imaging results, each rat was sacrificed after imaging. The heart was quickly excised and rinsed in saline. Two ml of pre-warmed TTC solution (0.5% in PBS, w/v, pH 7.4) was infused into the entire myocardium in a retrograde fashion via the aorta. TTC staining was allowed to continue for 15 min at 37° C., followed by a retrograde infusion of 10 ml of formaldehyde (4% v/v in PBS, pH 7.4). After 15 minutes, the fixed heart was sliced into consecutive slices of 0.5 mm each, and exposed to a storage phosphor screen (GE Healthcare). The autoradiograph was captured using a Storm 9200 phosphor imager (GE Healthcare). After an overnight de-staining in formaldehyde, the tissue slices were then photographed in the same orientation as the corresponding autoradiography.

Data processing. Using the autoradiography data, the radioactivity uptake ratio was determined between the area-at-risk and viable myocardium using the inbuilt analytical software on the Storm 9200 phosphor imager. Specifically, region of interests (ROIs) were placed on the area-at-risk and viable myocardium. The average signal intensity was determined in each ROI. The target-to-background ratio was calculated as the signal intensity in the area-at-risk divided by that of the normal myocardium. The data output was expressed as the ratio with standard deviation.

Figure 4:
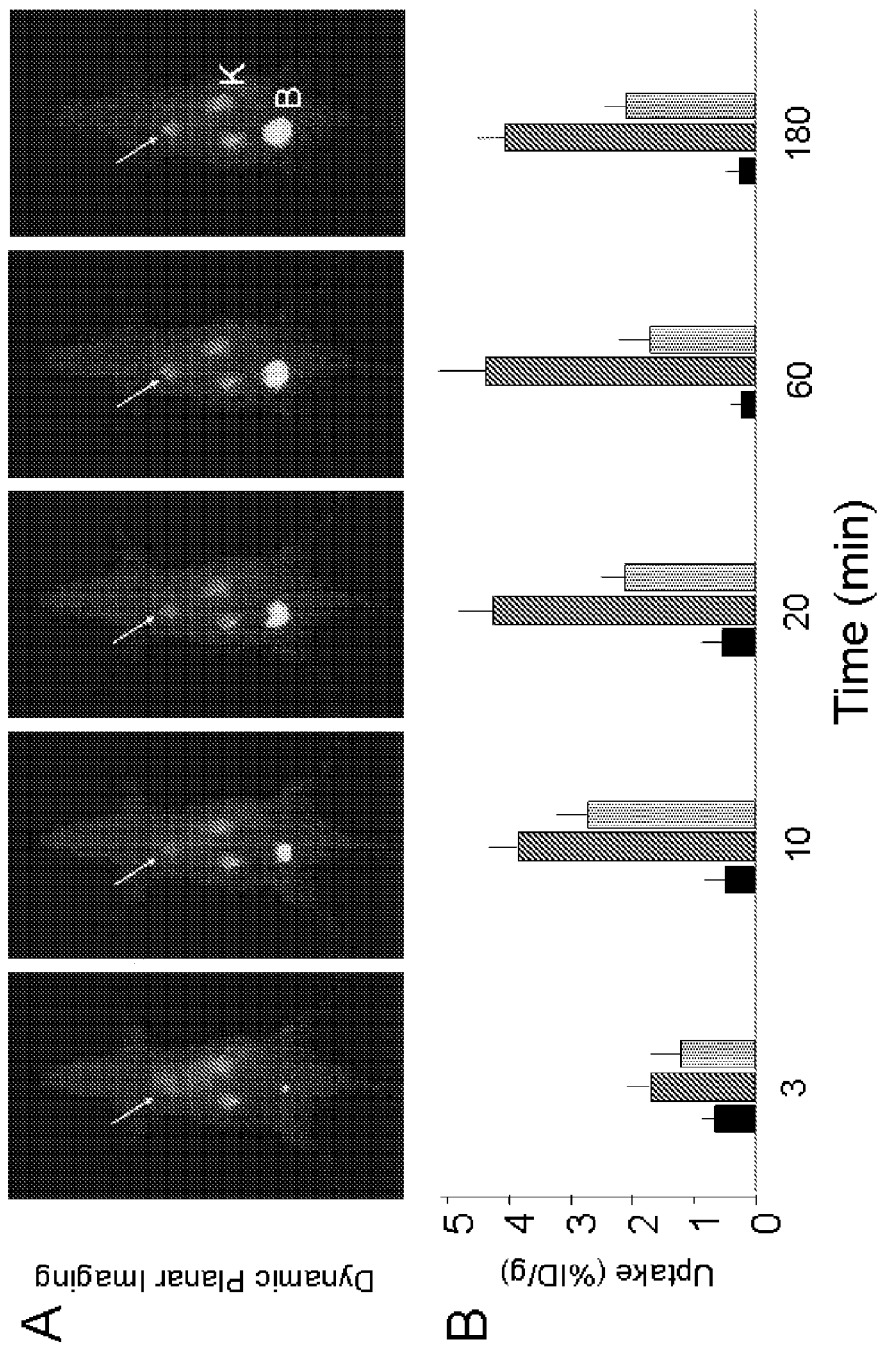
Figure 5:
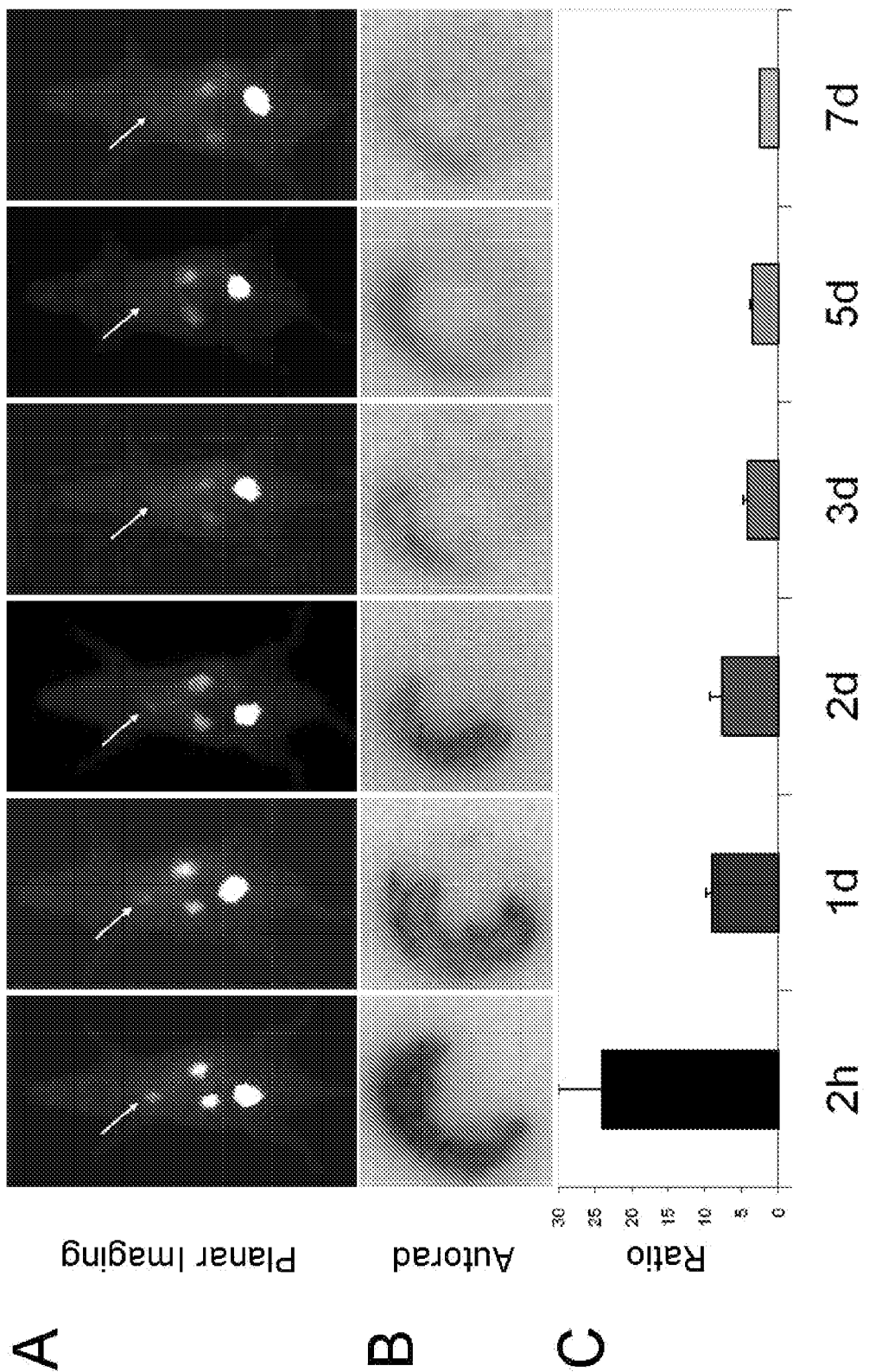
Figure 6:
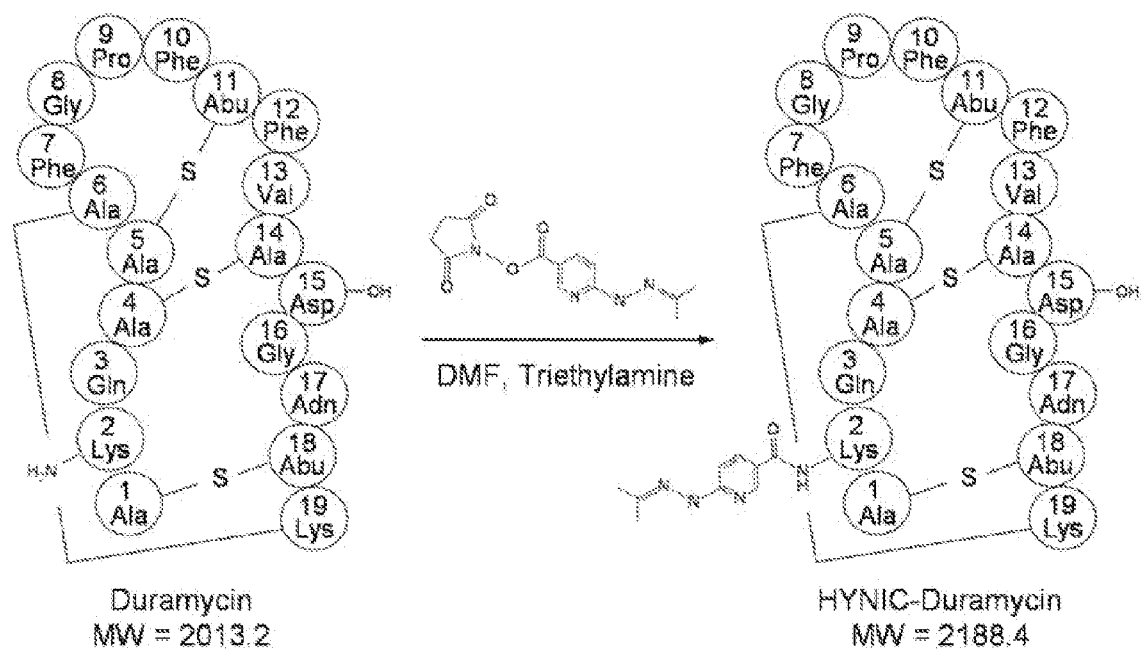
FIG. 6 shows the synthesis and structure of HYNIC modified duramycin.
Figure 7:
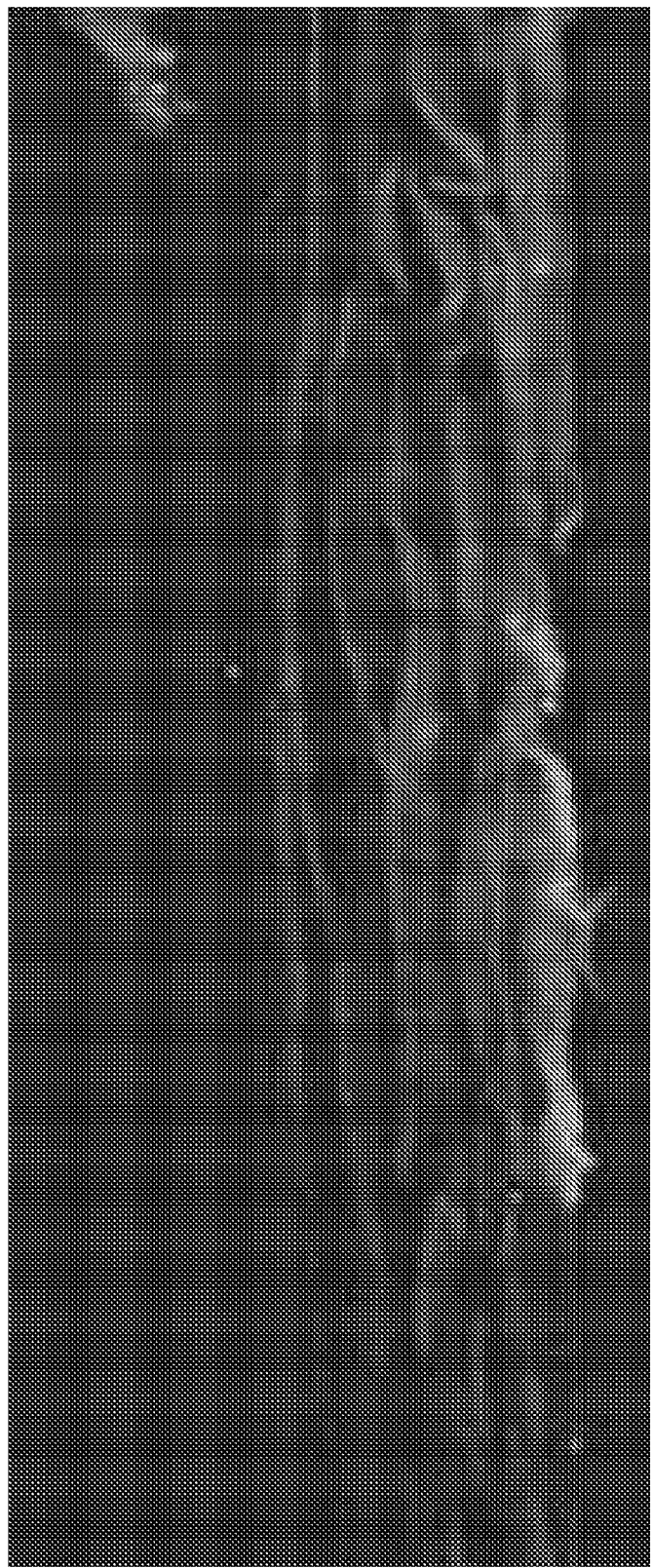
FIG. 7 shows fluorescent imaging of atherosclerosis plaques using $^{99m}$Tc-HYNIC-Duramycin.

Spatial and Temporal uptake of $^{99m}$Tc-HYNIC-Duramycin in the area-at-risk. The uptake kinetics of $^{99m}$Tc-HYNIC-Duramycin in the area-at-risk were characterized by measuring the level of radioactivity at different time points after injection and are summarized in FIG. 4. Quantitative uptake data from dissected heart tissues of the infarct, ischemic non-infarct, and normal myocardium at 3, 10, 20, 60 and 180 min after tracer injection are presented in FIG. 1A. Typical examples of whole-body anterior planar images acquired at the above time points are shown in FIG. 1B. After injection the radioactivity uptake in the infarcted myocardium rapidly rose to 1.8±0.4% ID/g within 3 min, and approached a plateau by 10 min at 4.3±0.7% ID/g. The radioactivity uptake in the infarct tissues remained persistent for at least 3 hours after injection without significant washout. In the meantime, the tracer uptake in the ischemic-non-infarct myocardium was also significant, and peaked at around 10 min post-injection at 2.7±0.6% ID/g. This was followed by a decline to a minimum of 1.6±0.6% ID/g at 60 min and a gradual increase to 2.1±0.3% ID at 180 min. The radioactivity uptake in the normal myocardium was low, reflecting the residual blood pool signal. According to the measurements using dissected heart tissues, at 60 min after injection, the average infarct-to-normal and ischemic-to-normal ratios were 31.9 and 11.1, respectively. The PE-dependent uptake of $^{99m}$Tc-HYNIC-Duramycin was confirmed using an inactivated tracer, $^{99m}$Tc-HYNIC-Duramycin$^I$, where the uptake kinetics was strikingly different. With a markedly lower rate of uptake, the presence of radioactivity after $^{99m}$Tc-HYNIC-Duramycin$^I$ injection in the infarcted tissue was reduced by ~60%, and it reached a much delayed maximum at about 30 min. Overall, the uptake of $^{99m}$Tc-HYNIC-Duramycin exhibited intense and rapid kinetics approaching a plateau within 10 minutes after injection. A greater uptake was correlated with more severe tissue damage in the area-at-risk. The radiotracer was sequestered in the irreversibly damaged myocardium, which is consistent with the high binding affinity and specificity of Duramycin-PE interactions.

Figure 2:
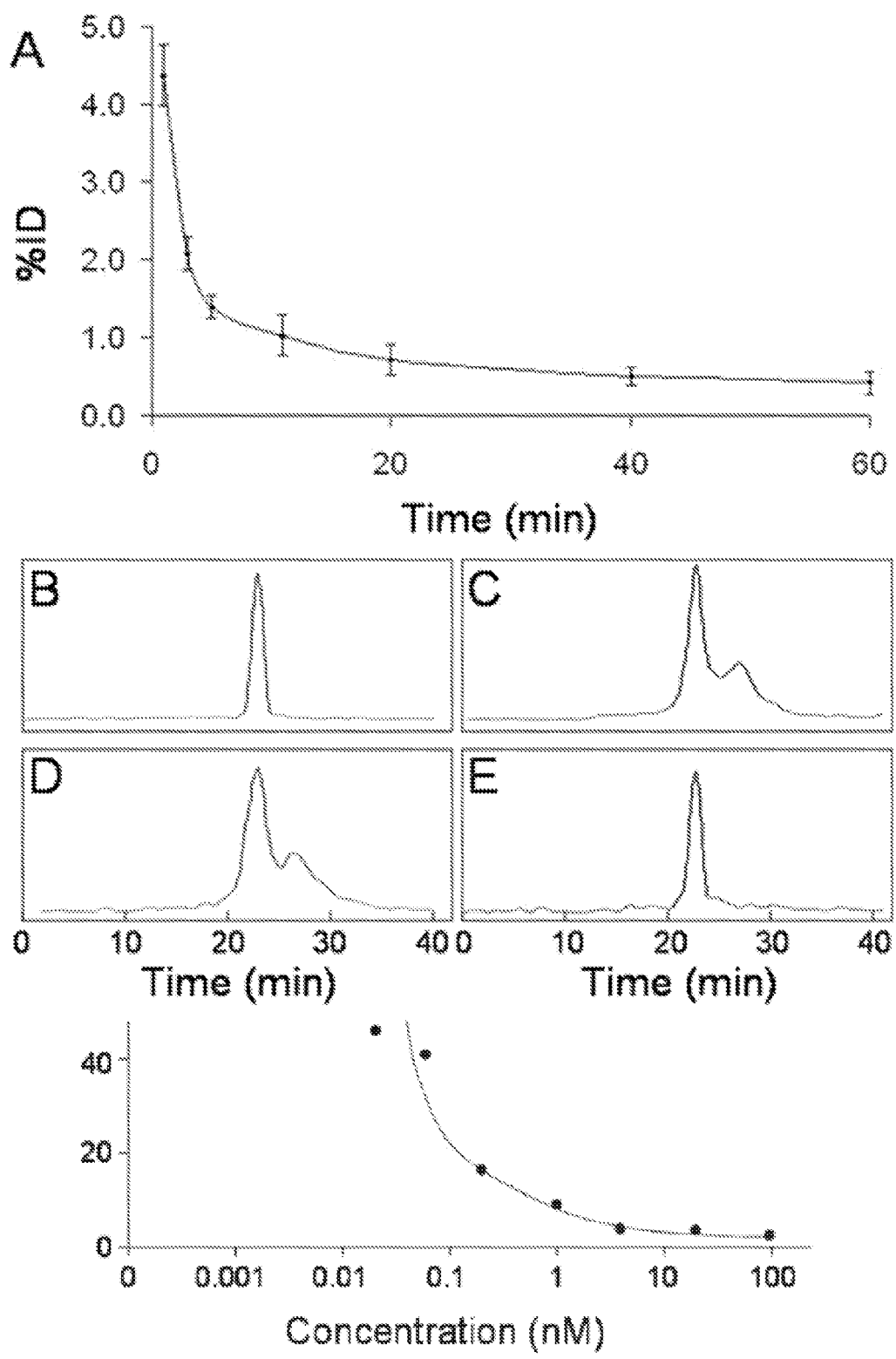

Window of Detection. With planar imaging, the window of detection for AMI using $^{99m}$Tc-HYNIC-Duramycin is about 48 hr after reperfusion. Well-defined focal uptake of the radiotracer was conspicuously seen with 2 and 24 hr-old infarct, and it remained visible by planar imaging at 48 hr. Typical planar images acquired at different time points after reperfusion are shown in FIG. 2A.

The in vivo planar imaging results were confirmed by ex vivo measurements using semi-quantitative storage phosphor autoradiography. (See FIG. 2B). There is a more homogeneous radioactivity uptake in the ischemic zone within a few hours after reperfusion. At 24 hr post infarction there is a tendency of having higher signal intensity at the periphery of the infarct region. This uptake profile was similar to the distribution of radiolabeled Annexin V and C2A in the ischemic zone presumably due to an obstruction of microvasculatures in the necrotic core and a continuous wave of cell death that propagates outward from the infarct center. (Machaidze G et al., Specific binding of Ro 09-0198 (cinnamycin) to phosphatidylethanolamine: a thermodynamic analysis, Biochemistry 2002; 41(6):1965-1971; Guder A et al., Posttranslationally modified bacteriocins—the lantibiotics, Biopolymers 2000; 55(1):62-73). Beyond 48 hr after reperfusion, the uptake of radioactivity in the infarct became much diminished and diffused, and was no longer discernable in planar images.

The signal-to-background ratios in the auto-radiographs were determined by measuring the average signal intensity at the ischemic region and in the normal myocardium. The ratios are summarized in FIG. 2C. Compared with 2 hr post infarction, the signal-to-background ratio declined by 32% at 24 hr and 43% at 48 hr. This was followed by a more substantial decrease in the signal-to-background ratio in the next a few days.

With only 19 amino acids, Duramycin is the smallest known polypeptide that has a defined 3-dimensional binding structure. Duramycin binds PtdE (PtdE) at a 1:1 ratio with high affinity and exclusive specificity. As an abundant binding target, PtdE is a major phospholipid and accounts for about 20% of the phospholipid content in mammalian cellular membranes. PtdE is externalized to the surface of apoptotic cells. PtdE also becomes accessible in necrotic cells due to compromised plasma membrane integrity. Given the unique physicochemical properties of Duramycin and the availability of PtdE in acute cell death, $^{99m}$Tc-HYNIC-Duramycin is a superior molecular probe for imaging PtdE.

Methods. Duramycin is covalently modified with succinimidyl 6-hydrazinonicotinate acetone hydrazone (HYNIC) and labeled with $^{99m}$Tc using a coordination chemistry involving tricine-phosphine co-ligands. The retention of PtdE-binding activities was confirmed using competition assays with PtdE-containing liposomes. The blood clearance, pharmacokinetics and biodistribution of $^{99m}$Tc-HYNIC-Duramycin were measured in rats. $^{99m}$Tc-HYNIC-Duramycin binding to acute cell death in vivo was also demonstrated using a rat model of acute myocardial infarction induced by ischemia and reperfusion, and it was confirmed using autoradiography and histology.

Results. HYNIC-derivatized Duramycin with 1:1 stoichiometry was synthesized and confirmed by mass spec. The radiolabeling efficiency was 80-85%, radiochemical purity was 78-89%, and the specific activity was 2×10$^5$ Ci/mole. The radiotracer was purified with radio HPLC before use. The specific uptake of $^{99m}$Tc-HYNIC-Duramycin in apoptotic cells was enhanced by more than 30 folds compared to viable control cells. This binding was competitively diminished in the presence of PtdE-containing liposomes but not by liposomes consisting of other phospholipid species. Intravenously injected $^{99m}$Tc-HYNIC-Duramycin demonstrated favorable pharmacokinetic and biodistribution profiles, and it quickly cleared from the circulation via the renal system with a blood half-life of less than 4 min in rats. The hepatic and gastrointestinal uptake was very low. $^{99m}$Tc-HYNIC-Duramycin is completely un-metabolized in vivo, and the intact agent is recovered from the urine. Combined with a fast clearance and low hepatic background, the avid binding of $^{99m}$Tc-HYNIC-Duramycin to the infarcted myocardium quickly becomes conspicuous shortly after injection. The uptake of radioactivity in infarct tissues was confirmed by autoradiography and histology.

$^{99m}$Tc-HYNIC-Duramycin is a stable, low molecular weight PtdE-binding radiopharmaceutical with favorable in vivo imaging profiles. It is a superior molecular probe for PtdE imaging.

$^{99m}$Tc-HYNIC-Duramycin is a low-molecular weight, fast-clearing radiopharmaceutical that detects apoptosis/necrosis by binding to PtdE.

Methods. Acute myocardial infarction was induced in rats. For uptake kinetics in the area-at-risk, the radioactivity was measured at 3, 10, 20, 60 and 180 min after injection. To estimate the window of detection, $^{99m}$Tc-HYNIC-Duramycin was injected at 0.1, 1, 2, 3, 5 and 7 days post infarction. Planar imaging and autoradiography were performed.

Results. $^{99m}$Tc-HYNIC-Duramycin uptake in the area-at-risk rapidly rose to ~4% ID/g without washout. The infarcts were conspicuously seen at 24 hr and remained detectable at 48 hr.

$^{99m}$Tc-HYNIC-Duramycin accumulates avidly and rapidly in infarct tissues in a PE-dependent fashion with a reasonably wide detection window.

---

I claim:

1. A radiopharmaceutical compound made by a process comprising:
   providing a polypeptide sequence set forth in SEQ. ID. No. 1 or a sequence having at least 70% sequence similarity to SEQ. ID. No. 1,
   wherein the polypeptide comprises a thioether bond between amino acids located at positions 1-18, 4-14, and 5-11,
   wherein the polypeptide comprises an amide bond between amino acids located at positions 6-19, and,
   wherein one or more distal moieties according to the structure

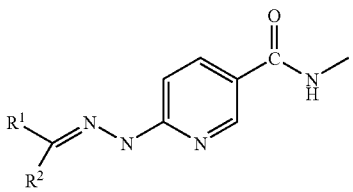

are covalently bound to the amino acid at position 1, position 2, or, positions 1 and 2 of the polypeptide, and,
   wherein $R^1$ and $R^2$ are each independently a straight or branched, saturated or unsaturated $C_{1-4}$ alkyl, and,
   chelating one or more of the distal moieties with $^{99m}Tc^x$, $(^{99m}Tc=O)^{+3}$, $(^{99m}Tc\equiv N)^{+2}$, $O=^{99m}Tc=O)^+$ or $(^{99m}Tc(CO)_3)^+$,
   wherein x is a redox or oxidation state selected from the group consisting of +7, +6, +5, +4, +3, +2, +1, 0 and −1, or, a salt, or hydrate thereof.

2. The radiopharmaceutical compound of claim 1, wherein $R^1$ is $CH_3$, and wherein $R^2$ is $CH_3$.

3. The radiopharmaceutical compound of claim 1, wherein the compound according to SEQ. ID. No. 1 is substituted with the distal moiety at position 1.

4. The radiopharmaceutical compound of claim 1, wherein the compound according to SEQ. ID. No. 1 is substituted with the distal moiety at position 2.

5. The radiopharmaceutical compound of claim 1, wherein the compound according to SEQ. ID. No. 1 is substituted with distal moieties at positions 1 and 2.

6. The radiopharmaceutical compound of claim 1, wherein amino acids located at positions 7, 10, or 12, or a combination thereof, are substituted with a hydrophobic amino acid selected from Val, Leu, Ile, Met, or Trp, or a combination thereof.

7. The radiopharmaceutical compound of claim 1, wherein amino acids located at positions 8, 13 or a combination thereof are substituted with a hydrophobic amino acid selected from Val, Leu, Ile, Met, or Phe, or a combination thereof.

8. The radiopharmaceutical compound of claim 1, wherein at least one amino acid residue located at positions 1-4 and 16-19 of the polypeptide are modified by at least one modifier selected from a N-hydroxysuccinimide ester, isothiocyanate, maleimide, biotin, glutathione, antibody, antigen, polymer, peptide, protein, complex, particle and liposome.

9. The radiopharmaceutical compound of claim 1, wherein the modified polypeptide substantially retains binding affinity and specificity towards phosphatidylethanolamine.

10. A pharmaceutical injectable dosage form comprising:
    the radiopharmaceutical compound of claim 1, and,
    an injectable carrier system.

11. A method of imaging cardiac apoptosis and/or necrosis, atherosclerotic plaque or acute myocardial infarct comprising:
    administering the pharmaceutical dosage form of claim 10 to a patient, and,
    imaging the gamma rays emitted by the $^{99m}Tc^x$.

12. A radiopharmaceutical compound made by a process comprising:
    providing a polypeptide sequence set forth in SEQ. ID. No. 1 or a sequence having at least 70% sequence similarity to SEQ. ID. No. 1,
    wherein the polypeptide comprises a thioether bond between amino acids located at positions 1-18, 4-14, and 5-11,
    wherein the polypeptide comprises an amide bond between amino acids located at positions 6-19, and,
    wherein one or more distal moieties according to the structure

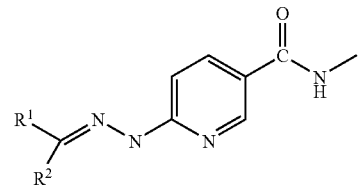

are covalently bound to the amino acid at position 1, position 2, or, positions 1 and 2 of the polypeptide, and,
    wherein $R^1$ and $R^2$ are each independently a straight or branched, saturated or unsaturated $C_{1-4}$ alkyl, and,
    chelating one or more of the distal moieties with an isotope selected from $^{111}In^{+3}$, $^{111}In^0$, $^{111}In^{-5}$, $^{125}I^{-1}$, $^{125}I^0$, $^{125}I^{+7}$, $^{131}I^{-1}$, $^{131}I^0$, $^{131}I^{+7}$, $^{18}F^{-1}$, $^{18}F^0$, $^{64}Cu^0$, $^{64}Cu^{+1}$, $^{64}Cu^{+2}$ or $^{64}Cu^{+3}$,
    or, a salt, or hydrate thereof.

13. A pharmaceutical injectable dosage form comprising:
    the radiopharmaceutical compound of claim 12, and,
    an injectable carrier system.

14. A method of imaging cardiac apoptosis and/or necrosis, atherosclerotic plaque or acute myocardial infarct comprising:
    administering the pharmaceutical dosage form of claim 13 to a patient, and,
    imaging the gamma rays emitted by the isotope.

15. A radiopharmaceutical compound made by a process comprising:
    providing a polypeptide sequence set forth in SEQ. ID. No. 1 or a sequence having at least 70% sequence similarity to SEQ. ID. No. 1,
    wherein the polypeptide comprises a thioether bond between amino acids located at positions 1-18, 4-14, and 5-11,
    wherein the polypeptide comprises an amide bond between amino acids located at positions 6-19, and,
    wherein one or more distal moieties according to the structure

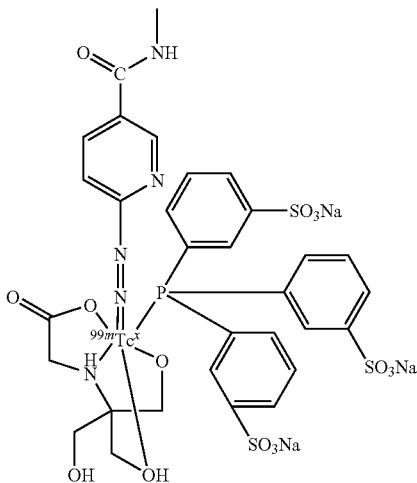

are covalently bound to the amino acid at position 1, position 2, or, positions 1 and 2 of the polypeptide, wherein x is a redox or oxidation state selected from the group consisting of +7, +6, +5, +4, +3, +2, +1, 0 and −1, or, a salt, or hydrate thereof.

16. The radiopharmaceutical compound of claim 15, wherein the compound according to SEQ. ID. No. 1 is substituted with the distal moiety at position 1.

17. The radiopharmaceutical compound of claim 15, wherein the compound according to SEQ. ID. No. 1 is substituted with the distal moiety at position 2.

18. The radiopharmaceutical compound of claim 15, wherein the compound according to SEQ. ID. No. 1 is substituted with distal moieties at positions 1 and 2.

19. The radiopharmaceutical compound of claim 15, wherein amino acids located at positions 7, 10, or 12, or a combination thereof, are substituted with a hydrophobic amino acid selected from Val, Leu, Ile, Met, or Trp, or a combination thereof.

20. The radiopharmaceutical compound of claim 15, wherein amino acids located at positions 8, 13 or a combination thereof are substituted with a hydrophobic amino acid selected from Val, Leu, Ile, Met, or Phe, or a combination thereof.

21. The radiopharmaceutical compound of claim 15, wherein at least one amino acid residue located at positions 1-4 and 16-19 of the polypeptide are modified by at least one modifier selected from a N-hydroxysuccinimide ester, isothiocyanate, maleimide, biotin, glutathione, antibody, antigen, polymer, peptide, protein, complex, particle and liposome.

22. The radiopharmaceutical compound of claim 15, wherein the modified polypeptide substantially retains binding affinity and specificity towards phosphatidylethanolamine.

23. A pharmaceutical injectable dosage form comprising:
the radiopharmaceutical compound of claim 15, and,
an injectable carrier system.

24. A method of imaging cardiac apoptosis and/or necrosis, atherosclerotic plaque or acute myocardial infarct comprising:
administering the pharmaceutical dosage form of claim 23 to a patient, and,
imaging the gamma rays emitted by the $^{99m}Tc^x$.

* * * * *